United States Patent
Day et al.

(10) Patent No.: US 10,617,815 B2
(45) Date of Patent: *Apr. 14, 2020

(54) PATIENT CARE SYSTEM WITH CONDITIONAL ALARM FORWARDING

(71) Applicant: ICU Medical, Inc., San Clemente, CA (US)

(72) Inventors: William Kenneth Day, Hoffman Estates, IL (US); Steve Joseph Lindo, Chicago, IL (US); Paul John Foryt, Woodstock, IL (US); Justin Joseph Schmidt, Grayslake, IL (US); Robert Cousineau, Boston, MA (US); Michael Kremliovsky, Poway, CA (US); Sumant Ramachandra, Northbrook, IL (US); Anatoly S. Belkin, Glenview, IL (US); Gary Mills, Escondido, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,272

(22) Filed: May 9, 2019

(65) Prior Publication Data

US 2020/0069865 A1 Mar. 5, 2020

Related U.S. Application Data

(63) Continuation of application No. 15/674,889, filed on Aug. 11, 2017, now Pat. No. 10,300,194, which is a
(Continued)

(51) Int. Cl.
*A61M 5/142* (2006.01)
*G16H 20/17* (2018.01)
(Continued)

(52) U.S. Cl.
CPC ......... *A61M 5/142* (2013.01); *G08B 21/0461* (2013.01); *G16H 20/17* (2018.01);
(Continued)

(58) Field of Classification Search
None
See application file for complete search history.

(56) References Cited

U.S. PATENT DOCUMENTS

| | | | |
|---|---|---|---|
| 5,319,363 A | * 6/1994 | Welch | H04Q 9/00 340/12.3 |
| 6,980,958 B1 | 12/2005 | Surwit et al. | |

(Continued)

FOREIGN PATENT DOCUMENTS

| | | |
|---|---|---|
| CA | 2 898 825 | 7/2014 |
| CO | 01110843 | 8/2003 |

(Continued)

OTHER PUBLICATIONS

"File Verification" Wikipedia.org, dated Oct. 11, 2011 in 2 pages, https://en.wikipedia.org/w/index.php?title=File_verification&oldid=455048290.

(Continued)

*Primary Examiner* — John F Mortell
(74) *Attorney, Agent, or Firm* — Knobbe Martens Olson & Bear, LLP

(57) ABSTRACT

A patient care system is disclosed that includes a medical device such as an infusion pump. The medical device generates a data message containing information such as the status of the therapy being delivered, operating data or both. An alarm generating system assesses the data message from the pump and generates an alarm message if certain conditions established by a first set of rules are met. The alarm message is assessed according to a second set of rules as to whether to suppress the alarm message. The data message
(Continued)

contains a required input for both the first and second algorithms. A dispatching system is adapted to forward the alarm message to an alarm destination according to a third set of rules. The alarm destination expresses an alarm upon receipt of the alarm message.

18 Claims, 10 Drawing Sheets

Related U.S. Application Data continuation of application No. 14/700,357, filed on Apr. 30, 2015, now Pat. No. 9,764,082.

(60) Provisional application No. 61/986,562, filed on Apr. 30, 2014.

(51) Int. Cl.
  *G16H 40/67* (2018.01)
  *G16H 40/63* (2018.01)
  *G08B 21/04* (2006.01)
  *G16H 50/70* (2018.01)

(52) U.S. Cl.
  CPC ............ *G16H 40/63* (2018.01); *G16H 40/67* (2018.01); *G16H 50/70* (2018.01); *A61M 2205/18* (2013.01); *A61M 2205/3553* (2013.01); *A61M 2205/3584* (2013.01); *A61M 2205/3592* (2013.01); *A61M 2205/52* (2013.01)

(56) References Cited

U.S. PATENT DOCUMENTS

| | | | |
|---|---|---|---|
| 7,519,905 B2 | 4/2009 | Kougiouris et al. | |
| 7,551,078 B2* | 6/2009 | Carlson | A61B 5/0002 340/539.12 |
| 8,489,427 B2 | 7/2013 | Simpson et al. | |
| 9,971,871 B2 | 5/2018 | Arrizza et al. | |
| 9,995,611 B2 | 6/2018 | Ruchti et al. | |
| 10,022,498 B2 | 7/2018 | Ruchti et al. | |
| 10,042,986 B2 | 8/2018 | Ruchti et al. | |
| 10,046,112 B2 | 8/2018 | Oruklu et al. | |
| 10,166,328 B2 | 1/2019 | Oruklu et al. | |
| 10,238,799 B2 | 3/2019 | Kohlbrecher | |
| 10,238,801 B2 | 3/2019 | Wehba et al. | |
| 10,242,060 B2 | 3/2019 | Butler et al. | |
| 10,300,194 B2 | 5/2019 | Day et al. | |
| 10,311,972 B2 | 6/2019 | Kohlbrecher et al. | |
| 10,314,974 B2 | 6/2019 | Day et al. | |
| 10,333,843 B2 | 6/2019 | Jha et al. | |
| 2001/0048027 A1 | 12/2001 | Walsh | |
| 2002/0143580 A1 | 10/2002 | Bristol et al. | |
| 2002/0173702 A1 | 11/2002 | Lebel et al. | |
| 2003/0014817 A1 | 1/2003 | Gallant et al. | |
| 2004/0104271 A1 | 6/2004 | Martucci et al. | |
| 2005/0102165 A1 | 5/2005 | Oshita et al. | |
| 2007/0229249 A1* | 10/2007 | McNeal | A61B 5/0002 340/524 |
| 2008/0154177 A1* | 6/2008 | Moubayed | G06F 19/3468 604/19 |
| 2008/0300572 A1* | 12/2008 | Rankers | A61B 5/14532 604/504 |
| 2009/0270833 A1* | 10/2009 | DeBelser | A61M 5/16831 604/500 |
| 2010/0209268 A1 | 8/2010 | Davis | |
| 2011/0138185 A1 | 6/2011 | Ju et al. | |
| 2011/0231216 A1 | 9/2011 | Fyke et al. | |
| 2013/0204188 A1 | 8/2013 | Kamen et al. | |
| 2013/0275539 A1* | 10/2013 | Gross | H04L 12/1895 709/206 |
| 2014/0163517 A1 | 6/2014 | Finan et al. | |
| 2014/0266790 A1 | 9/2014 | Al-Ali et al. | |
| 2016/0015885 A1 | 1/2016 | Pananen et al. | |
| 2019/0096518 A1 | 3/2019 | Pace | |
| 2019/0147998 A1 | 5/2019 | Ruchti et al. | |
| 2019/0228863 A1 | 7/2019 | Dharwad et al. | |
| 2019/0240405 A1 | 8/2019 | Wehba et al. | |
| 2019/0243829 A1 | 8/2019 | Butler et al. | |

FOREIGN PATENT DOCUMENTS

| | | |
|---|---|---|
| JP | 07-502678 | 3/1995 |
| JP | 11-500643 | 1/1999 |
| JP | 2000-316820 | 11/2000 |
| JP | 2002-531154 | 9/2002 |
| JP | 2006-520949 | 9/2006 |
| JP | 2007-518479 | 7/2007 |
| JP | 2008-080036 | 4/2008 |
| JP | 2008-516303 | 5/2008 |
| JP | 2008-529675 | 8/2008 |
| JP | 2009-163534 | 7/2009 |
| JP | 2010-502361 | 1/2010 |
| JP | 2012-070991 | 4/2012 |
| WO | WO 2015/124569 | 8/2015 |

OTHER PUBLICATIONS

Gabel et al., "Camp: A Common API for Measuring Performance", 21st Large Installations System Administration Conference (LISA '07), 2007, pp. 49-61.

"Software Versioning" Wikipedia.org, dated Oct. 16, 2011 in 11 pages, https://en.wikipedia.org/w/index.php?title=Software_versioning&oldid=455859110.

Sutton et al., "The Syntax and Semantics of the PROforma Guideline Modeling Language", Journal of the American Medical Informatics Association, Sep./Oct. 2003, vol. 10, No. 5, pp. 433-443.

\* cited by examiner

PATIENT CARE SYSTEM WITH CONDITIONAL ALARM FORWARDING

CROSS-REFERENCE TO RELATED APPLICATIONS

This application is a continuation of U.S. patent application Ser. No. 15/674,889, entitled "Patient Care System with Conditional Alarm Forwarding," filed Aug. 11, 2017, which is a continuation of U.S. patent application Ser. No. 14/700,357, entitled "Patient Care System with Conditional Alarm Forwarding," filed Apr. 30, 2015, which claims the benefit of priority to U.S. Provisional Patent Application No. 61/986,562, entitled "Patient Care System with Conditional Alarm Forwarding," filed Apr. 30, 2014, the disclosures of which are hereby incorporated by reference in their entirety.

BACKGROUND

Modern medical care often involves the use of medication management systems that include medication delivery and monitoring devices such as medication delivery pumps or patient parameter monitors or both, Medication management systems for configuring, controlling and monitoring medication delivery devices have been disclosed. For example, commonly owned U.S. Pat. No. 7,895,053 titled "MEDICATION MANAGEMENT SYSTEM" that issued on Feb. 22, 2011 and U.S. patent application Ser. No. 10/783,573 titled "MEDICATION MANAGEMENT SYSTEM" that published as US20050278194A1 on Dec. 15, 2005 disclose a medication management system wherein user customizable drug library or medical device configuration information is prepared using a drug library editor (DLE) program and module of a medication management unit (MMU). Hospira MedNet™ Meds™ software available from Hospira, Inc. of Lake Forest, Ill., U.S.A. includes such a DLE program. The MMU, which is equipped with Hospira MedNet™ Server software, downloads the customizable drug library to the medication delivery pump and receives status or activity information from the pump. Commonly owned U.S. Pat. No. 8,065,161 titled "SYSTEM FOR MAINTAINING DRUG INFORMATION AND COMMUNICATING WITH MEDICATION DELIVERY DEVICES" that issued on Nov. 22, 2011 discloses how the drug library or medical device configuration information is created, edited, stored and communicated to a medication delivery device in the context of a medication management system to deliver substances, such as fluids or fluid medication or both to patients.

According to the above-mentioned commonly owned published patent applications, a typical medication management system includes a point of care computer, such as a barcode point of care computer and/or pharmacy computer, and/or an MMU, in communication with one or more medication delivery devices. The point of care computer(s) and/or the MMU, with associated memory, store and share or communicate various information, such as patient information, prescription information, customized drug library or other information, for managing medication delivery to a patients, such as performing five-rights checking, configuring the medication delivery devices, and receiving and storing event, status or activity information received from the medication delivery devices.

Caregivers and clinicians use outputs from patient monitoring and equipment monitoring devices to make various patient care decisions. Patient monitoring devices and patient care equipment monitoring devices may be connected to a receiver, which receives the output signals from the patient monitoring devices and patient care equipment monitoring devices. In some cases, the receivers may display and/or record the information from the patient and patient care equipment monitoring devices. In other cases, the devices may include a monitor and/or recording medium. The receivers or devices may also have preset or adjustable alarms that are triggered when one of the outputs from the patient or patient care equipment monitoring devices deviates from a pre-set limit.

In hospitals that use infusion pumps and other medical devices, alarms are used to indicate device malfunction, therapy interruptions, end of therapy and other events that need to be handled by the clinical staff. Typically, alarms get displayed on device screens and produce audible sound. In some cases, there are too many devices that alarm in close proximity to each other. As a result, it is very hard to tell which device is actually alarming. The sound of alarms can also disturb or wake up sleeping patients. Hospital nurses usually manage multiple infusions running on multiple patients in one or more given clinical care areas. It is difficult for a nurse to be in the same vicinity of the infusion device at all times during an infusion, thus making it difficult to respond immediately to infusion-related or infusion device alarms. Further, clinical staff is not always in the close proximity to the alarming device to hear the alarm. In such situations it would be desirable for the staff to be notified of device alarms as soon as possible regardless of their proximity to the device so that they can better attend to their patients' needs.

Further, in some patient cases, it is critical to isolate the patient and reduce the exposure of the patient to unnecessary hospital conditions (e.g. burn patient being exposed to drafts or airborne contaminants when opening the door to the patient room). Further, multiple nurses may utilize the same pump on a patient between device cleaning. This results in an increase possibility of contamination due to an increased number of clinicians contacting the device. The pump may be contaminated by a clinician. This contamination may be transferred to the patient either by the clinician that first contaminated the pump or by a subsequent clinician who acquires the contamination by contacting the pump and then who transfers the contamination to the patient in the course of providing care to the patient. Further, contamination applied to a pump may be transferred to other devices and patients by clinicians who come in contact with the contamination on the pump and carry it with them to other pumps and patients where the contamination can be deposited and spread. Where alarms require a clinician to actually come to and contact a pump in order to assess the alarm, shut the alarm off or otherwise respond to the alarm, the likelihood of such contamination and cross-contamination increases.

SUMMARY OF THE INVENTION

A patient care system is disclosed that, in a preferred embodiment, includes at least one medical device such as an infusion pump. Each pump is capable of generating a data message containing information regarding the pump including the status of the therapy being delivered, operating data or both. The patient care system includes an alarm generating system that received the data message from the pump. The alarm generating system assesses the data message from the pump and fires a trigger if certain conditions established by a first set of rules, algorithms or instructions are met. The firing of a trigger produces an alarm message. This alarm message is assessed according to a second set of rules, algorithms or instructions as to whether to suppress the alarm message. For both the first and second algorithms, information generated by each pump is a required input.

The patient care system also includes a dispatching system that is connected to the alarm generating system. The dispatching system is adapted to forward the alarm message to an alarm destination according to a third set of rules, algorithms or instructions. Further, the patient care system includes an alarm destination connected to the dispatching system, the alarm destination expressing an alarm upon receipt by the alarm destination of the alarm.

In an alternate embodiment of the patient care system, the medical device is not part of the patient care system. Instead, the patient care system as disclosed interacts with the medical device. In another alternate embodiment of the patient care system, then alarm destination is not part of the patient care system but instead interacts with the patient care system. In yet another alternate embodiment of the patient care system, both the medical device and alarm destination are not part of the patient care system but instead interact with the patient care system. In yet another embodiment of the patient care system, both including and excluding the medical device and alarm destination or both, the alarm generating system and the dispatching system are combined into a single system.

DETAILED DESCRIPTION OF THE PREFERRED EMBODIMENT

Figure 1:
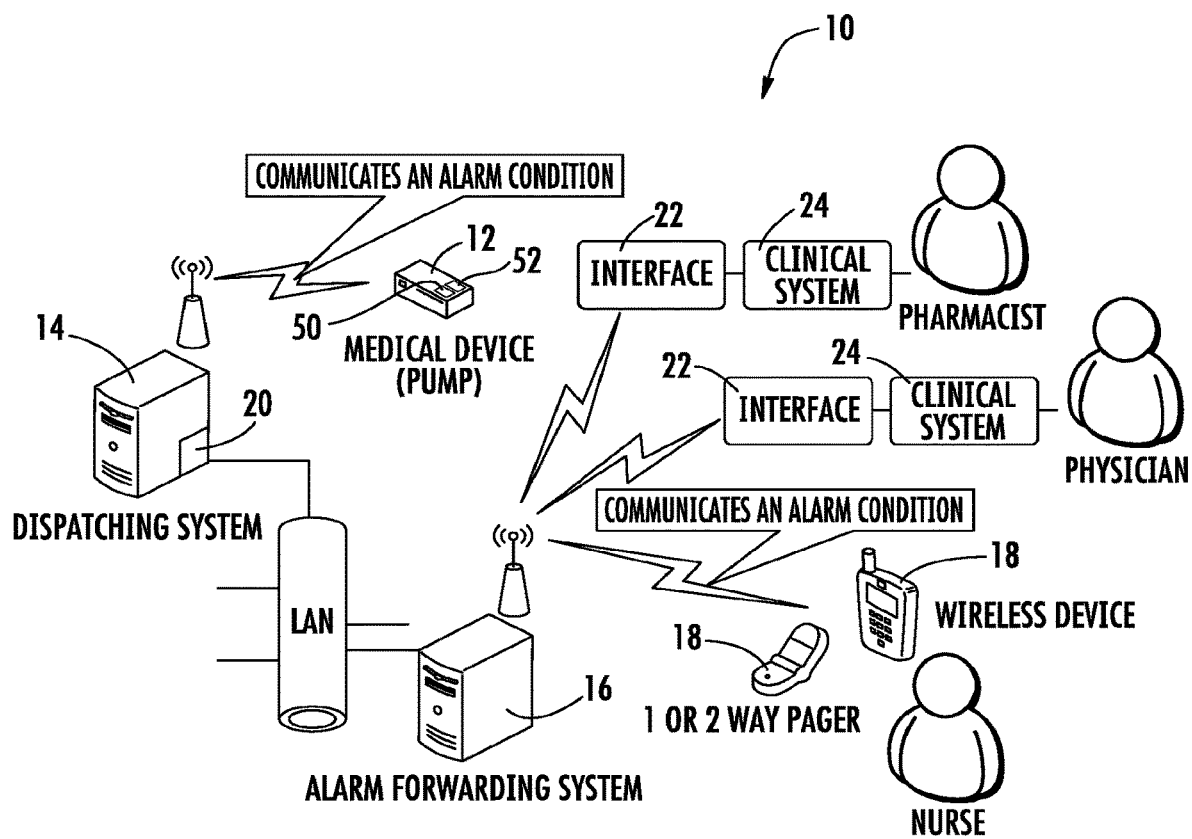
FIG. 1 is a schematic drawing of the architecture of one embodiment of a patient care system.

Referring to the Figures, a patient care system is shown in the Figures generally referred to by the reference number 10. The patient care system 10 interacts with a medical device 12 to manage alarms produced by the medical device 12. The patient care system 10 includes a dispatching system 14, an alarm forwarding system 16 and, in certain embodiments, a monitor/controlling system 18.

The patient care system 10 is intended to be deployed in any hospital or other facility that utilizes medical devices 12, including but not limited to infusion pumps, that are connected to networks either via hardwiring or through wireless connections. Such networks may be specific to the connection of one or more pumps 12 to each other or to control or monitoring devices. The networks may connect many medical devices and allow control or monitoring of a variety of such devices including control or monitoring from and to remote locations.

Medical device 12 is preferably an infusion pump 12 capable of receiving programming data from a nurse or other practitioner. Further, pump 12 is preferably capable of having its operational infusion program reviewed or confirmed or both by the nurse or other practitioner. Examples of pump 12 are the PLUM A+™ infusion system, LIFECARE PCA™ infusion system and SAPPHIRE™ infusion system sold by Hospira, Inc. of Lake Forest, Ill. Although medical device 12 is preferably an infusion pump 12, pump 12 as applied to the present patient care system 10 is intended to be understood to be any medical pump and more broadly, any medical device that has the capability of producing data and being connectable to a dispatching system 14 as described herein. Each pump 12 or other medical device is capable of generating a data message containing information regarding the pump including the status of the therapy being delivered, operating data or both. Examples of the data message generated by the pump 12 include, but are not limited to, pump 12 status data, the status of the therapy being delivered by the pump 12, event data associated with the pump 12 (e.g., expiration of certain time periods) and alarms associated with pump 12 or the delivery of therapy by the pump 12. Further, in some embodiments, pump 12 includes a local delay timer 50. The local delay timer may be a mechanical timer or a timer implemented in software. The local delay timer 50 is activated and begins counting when an alarm condition message is sent by the pump 12 to the dispatching system 14. In other embodiments of pump 12, pump 12 includes logic 52 that can be either discrete or implemented through software. Logic 52 allows pump 12 to make evaluations or take actions according to programming including rules, algorithms or instructions implemented on or associated with the logic 52 and may, in certain embodiments, also provide the local delay timer 50.

Dispatching system 14 is preferably a network application that manages alarms and preferably includes a dispatching server 20 capable of running software. A key function of the dispatching system 14 is to facilitate alarm management from the pump 12 to one of more alarm destinations (e.g., monitor/controlling systems 18) and back. For example, in a preferred embodiment, the dispatching system 14 is adapted to forward the alarm messages from the pump 12 to one or more monitor/controlling systems 18 according to a set of rules, algorithms or instructions. In a preferred embodiment of the patient care system 10, these rules, algorithms or instructions are executed on the alarm forwarding system 16 which, in effect, orchestrates the alarm flow from the pump 12 to one or more monitor/controlling systems 18 and back in order to implement safe, secure and reliable alarm handling. In a variant of this embodiment, rules, algorithms or instructions may be implemented on the pump 12 itself. The rules, algorithms or instructions can be configured by a rule editor.

In one embodiment, the dispatching server 14 incorporates an alarm forwarding system 16 that separates the alarm communication from the actual means of communication and forwards alarm information to monitor/controlling systems 18 according to rules, algorithms or instructions. The alarm forwarding system 16 assesses data messages produced by the pump 12 that are passed from the pump 12 to the alarm forwarding system 16 by the dispatching system 14 and fires a trigger if certain conditions established by a first set of rules, algorithms or instructions are met. The firing of a trigger produces an alarm message that is assessed according to a second set of rules, algorithms or instructions as to whether to suppress the alarm message. An example of a dispatching server 14 is a server equipped with the Hospira MedNet™ medication management software manufactured and sold by Hospira, Inc. of Lake Forest, Ill. The dispatching server can be used in combination with a hospital's existing alarm forwarding system or can be used in combination with a hospital's alarm forwarding system that has been modified to interface with the alarm messages received from dispatching server 14. In a preferred embodiment of the patient care system 10, the dispatching system 14 and alarm forwarding system 16 are separate systems that are connected together, for example, by a local area network (LAN) or wide area network (WAN), whether wireless, hardwired or connected by optical fibers, or any other communication protocol or system. However, the dispatching system 14 and alarm forwarding system 16 can be combined into a single system that performs the functions of the dispatching system 14 and alarm forwarding system 16 as described herein.

The patient care system 10, in a preferred embodiment, includes one or more monitor/controlling systems 18 connected to the dispatching system 14. The function of the monitor/controlling system 18 is to connect to the dispatching system 14, receive alarms and data from the dispatching system 14, communicate such alarms and data to a clinician and, in some embodiments, allow a clinician to produce a response to such alarms and data and otherwise produce acknowledgment or control responses and communicate such responses and acknowledgments to the dispatching system 14. The monitor/controlling system 18 preferably expresses an alarm upon receipt by the monitor/controlling system 18 of an alarm notification. The alarm can take various forms, including but not limited to an audible, visual, or vibratory alarm. The list of possible monitor/controlling systems 18 includes, but is not limited to, mobile wireless devices, network connected workstations, laptop computers, tablets, electronic mail, text messages, pagers and even fax machines In an embodiment of the patient care system 10, medical device 12 forwards a data message to dispatching system 14, and dispatching system 14 accesses the data message to determine if an alarm condition is met and if an escalated alarm should be suppressed. For example, a local alarm at the medical device 12 could be temporarily suppressed while an alarm is sent to a remote monitor/controlling system 18. The content of the data message could be a required input for the evaluation of both whether or not an alarm condition is met, and if the escalated alarm should be suppressed. As mentioned above, the data message could contain information regarding pump therapy status data, pump operating point data, or both pump therapy status data and pump operating point data. If an alarm condition is met, dispatching system 14 could cause alarm forwarding system 16 to forward an alarm message to one or more monitor/control systems 18. As a result, the monitor/controlling system 18 does not sound the alarm at the monitor/controlling system 18 except under certain predetermined conditions. Further, the medical device 12 itself may not sound an alarm except according to certain predetermined conditions.

Figure 2:
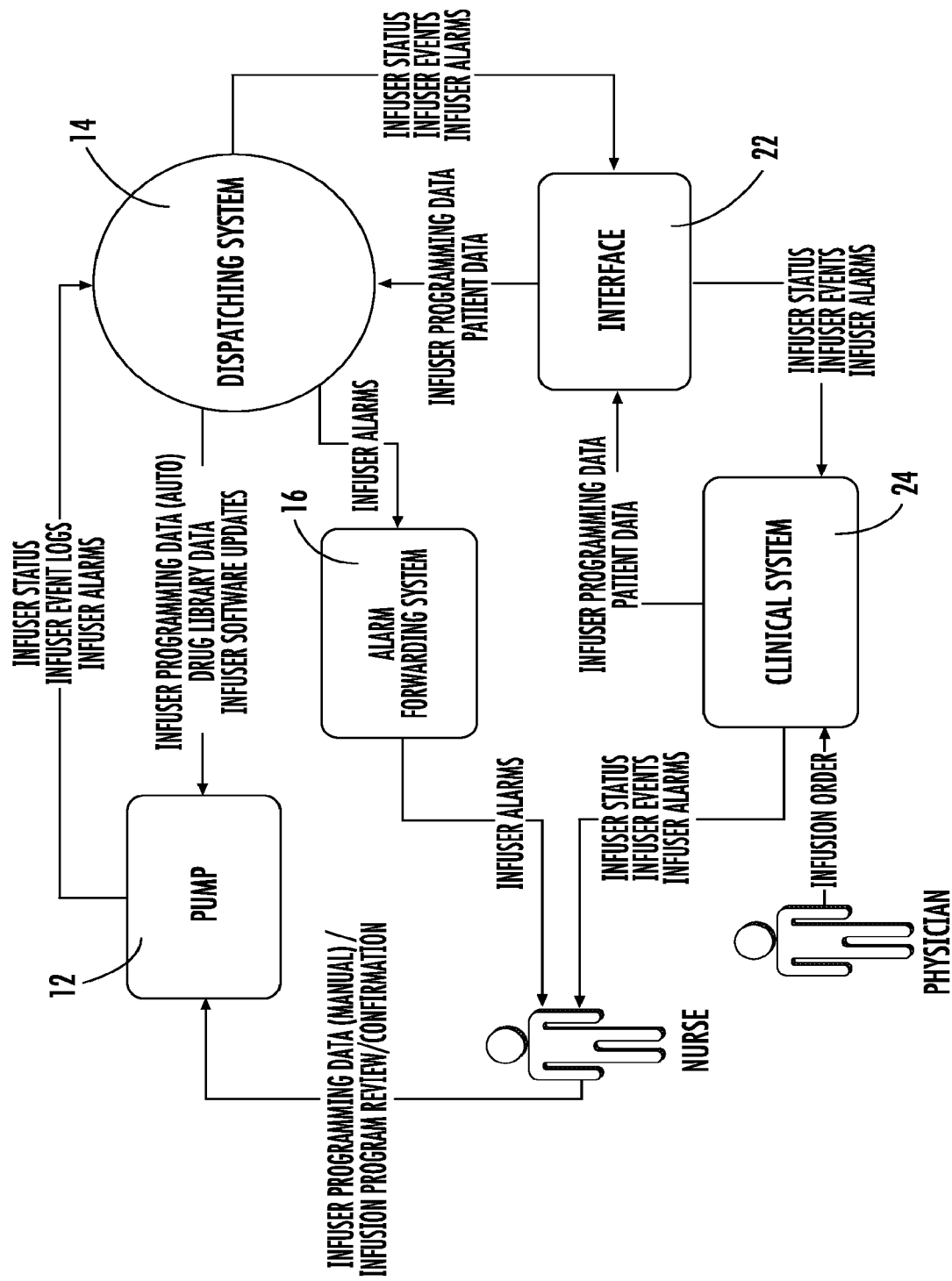
FIG. 2 is a data flow chart of one embodiment of a patient care system.

FIG. 2 shows an alarm condition being sent to the nurse and pharmacist to aid in their workflow (e.g., the nurse will pick up the next package of medication from the pharmacist and the pharmacist is informed that the infusion is nearing completion, which is the cue to prepare for the nurse to come and get the next package of medication for infusion). As can be seen in the embodiment shown in FIG. 2, pump 12 is in communication with the dispatching system 14 so that pump 12 sends status data about pump 12 to the dispatching system 14. Such status data includes, but is not limited to, patient biometric, physiological or medical parameter information, the location of pump 12 and the type and amount of medication administered by the pump 12. In addition, pump 12 sends event data to the dispatching system 14. Such event data includes, but is not limited to, information indicating that the infusion is nearing completion. Further, pump 12 sends alarm data to the dispatching system 14. Alarm data, as used in this specification, means all notifications that can benefit physicians, clinical staff or patients in handling the operation and safety of the pump 12.

Although the patient care system 10 described herein interacts with one or more pumps 12, the pumps 12 are not required to be part of the patient care system 10. However, as described hereafter, various aspects of the functionality of the patient care system 10 may be shared with the pump 12 so that in some embodiments the pump 12 may be part of the patient care system 10.

Besides receiving data from a pump 12, the dispatching system 14 may also send programming data to the pump 12. Such programming data may reconfigure the parameters and operation of the pump 12 with respect to both infusing of medication by the pump 12 and the type, amount and frequency of data gathered by the pump 12 and sent to the dispatching system 14. Further, dispatching system 14 may also send drug library data to the pump 12 which may then be used by pump 12 to configure limits and infuser settings to be used in the infusion of medication to the patient. In addition, the dispatching system 14 may send software updates to the pump 12 so that pump 12 has the most current software for its operations.

Dispatching system 14 interacts with alarm forwarding system 16 to forward alarms generated by the dispatching system 14 according to the appropriate recipient according to rules, algorithms or instructions. These rules, algorithms or instructions can, in part, be based on or take into consideration the clinical care area (CCA), patient identification, alarm priority, location of the pump 12 and the type of drug being infused by the pump 12. The rules, algorithms or instructions can be fixed and predetermined or can be customizable by the hospital or healthcare facility according to their own preferred practice or other practices recommended by others. An example of an appropriate recipient is the nurse who is caring for a patient that is receiving therapy from a pump 12. Further, where the alarms are sent to appropriate recipients, who that recipient is or the location where the alarm was forwarded may also be indicated or displayed on the pump 12 itself Dispatching system 14 may also communicate data, raw or processed by the dispatching system 14, to a clinical system 24 through an interface 22. Interface 22 provides a connection between the dispatching system 14 and a clinical system 24. The clinical system 24 may be another network (separate or interconnected with the network of dispatching system 14) where such network communicates information to the appropriate recipients such as the nurse having supervisory responsibility for the nurse caring for a patient that is receiving therapy from a pump 12, a physician overseeing the care of the patient, a pharmacist preparing medication for the patient or any combination of these or others having a need to know the status of the infusion therapy being applied to a patient through a pump 12. Examples of the data that can be communicated from the dispatching system 14 to and from the clinical system 24 via the interface 22 and from the clinical system 24 to an appropriate recipient includes, but is not limited to, the raw data produced by the pump 12 such as pump status data, pump event data and alarms associated with pump 12 or rules, results and data that has been processed by the dispatching system 14 or alarm forwarding system 16.

Further, the clinical system 24 allows appropriate personnel, such as the physician overseeing the care of the patient, to interface with and ultimately control or change the operation of the pump 12. For example, a physician through the clinical system 24 could modify the infusion parameters of the pump 12 by sending an infusion order to the clinical system 24 that passes through the interface 22, dispatching system 14 and ultimately to the pump 12. Further, new or modified programming data for the pump 12 may be entered into the clinical system 24, passed through the interface 22 to the dispatching system 14 and ultimately to the pump 12 where the current programming of pump 12 is either modified or replaced, preferably in an automated and/or remote manner.

Interface 22 likewise allows appropriate personnel to administer the rules used to control alarm forwarding in the system via a rule editor available on monitor/control device 18 or clinical system 24. The administration interface would allow the hospital personnel to determine rules for what contents from a data message from pump 12 would cause an alarm message to be generated. For example, an administrator could determine that an alarm would be generated whenever a certain kind of medication was interrupted, even if only temporarily, while the interruption of a different kind of medication did not generate an alarm unless the interruption was of a sufficient duration. The administration interface could also allow the hospital personnel to determine rules for what contents from a data message from pump 12 would control how and if certain alarm messages would be suppressed. For example, an administrator could determine that an alarm message generated based on a data message regarding a life critical or otherwise high risk drug, such as analgesics, sedatives or anticoagulants like Heparin for example, would not be suppressed at all, an alarm message generated based on a data message regarding a less critical drug could be locally suppressed at the device but could not be cleared remotely, and an alarm message generated based on a data message regarding a noncritical drug could be both locally suppressed at the device and cleared remotely.

Figure 3:
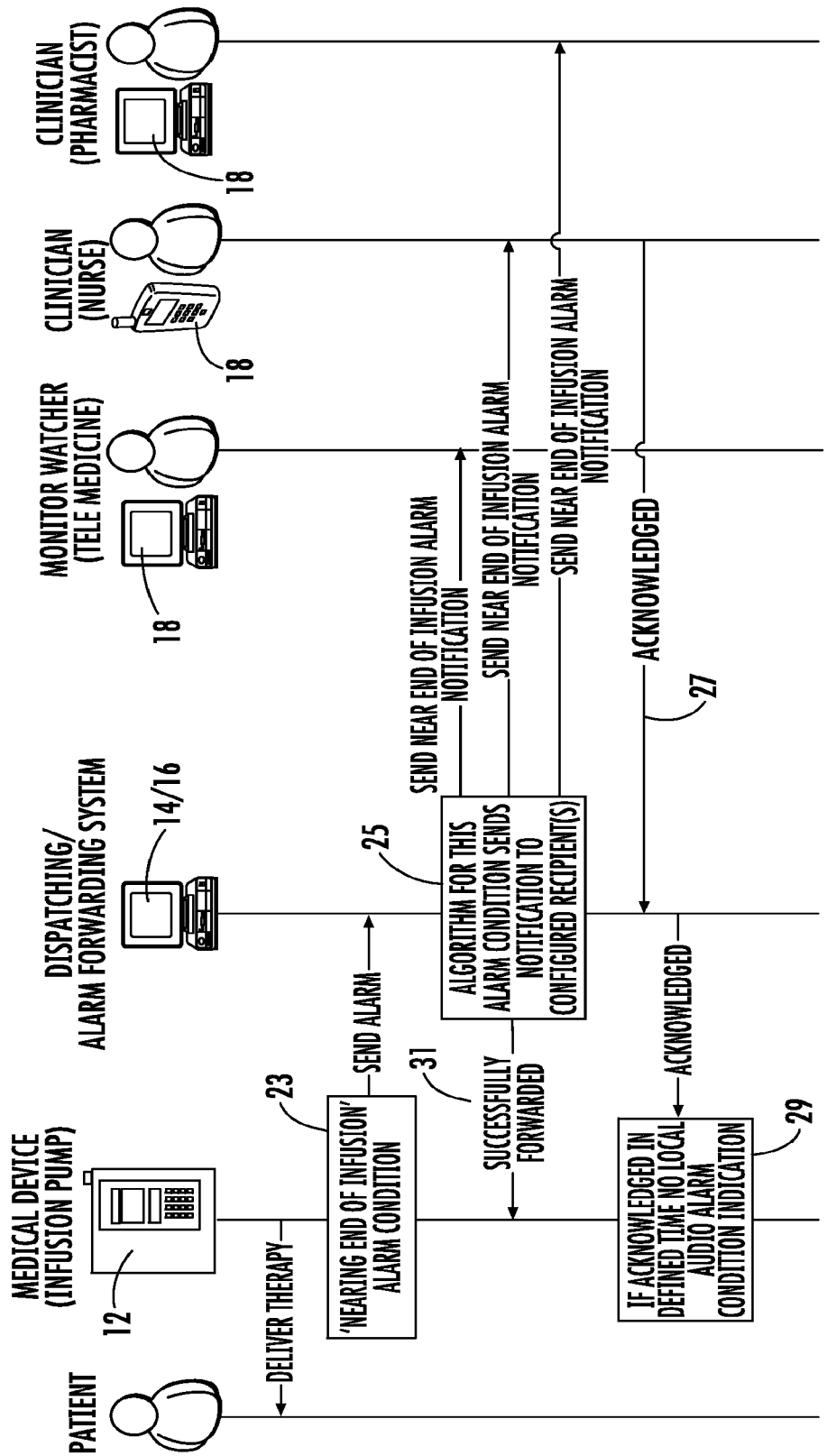
FIG. 3 is a chart showing the flow of information between various personnel and components of the patient care system of FIG. 1.

An example of how information flows in patient care system 10 can be described with references to FIG. 3. The main communication nodes in FIG. 3 include pump 12, dispatching system 14, alarm forwarding system 16, alarm destinations or monitor/controlling systems 18, the patient, nurse, telemedicine personnel, and pharmacist. As can be seen, an exemplary alarm condition 23, "Nearing the End of Infusion," is communicated from the pump 12 to the dispatching system 14. The dispatching system 14, operating according to an algorithm 25 for this alarm condition, sends the "Nearing the End of Infusion" alarm 23 to the alarm forwarding system 16, which broadcasts, according to its rules or algorithms 25 to the monitor/controlling system 18 and clinical system 24 through the interface 22 (FIG. 2).

Alternatively or in addition, the dispatching system 14 can send the alarm 23 to the interface 22 where it is subsequently passed to the clinical system 24 where it passes to the appropriate personnel such as the nurse, pharmacist or physician. In this way, multiple alarm messages are sent in parallel to the appropriate personnel according to the operation of the algorithm 25 operating on the dispatching system 14. Further, in a variant of this embodiment, an initial alarm message may be forwarded from a recipient of such alarm message to another person not initially sent the alarm message in a so-called "serial forwarding" fashion. Further, to avoid the same alarm being received by multiple devices at different times, which could give the mistaken impression that there are more alarms than there actual are, alarm messages can be synchronized when dispatched to multiple recipients (e.g., various monitor/controlling systems 18 such as a mobile tablet and a nurse station) so that the alarm messages arrive at the same time.

The administration interface could also be used to control how certain alarm messages flowed in patient care system 10. For example, the rules applied to alarm messages by alarm forwarding system 16 could be configurable so that alarm messages pertaining to life critical drugs were forwarded to various monitor/controlling systems 18 in parallel while alarm messages pertaining to less critical drugs were forwarded to a single monitoring system 18 and serially forwarded to another monitoring system 18 only in the event that the alarm was not acknowledged.

As can also be seen, the dispatching system 14 may receive an acknowledgment message 27 from the appropriate personnel, in this case, the nurse. Upon receipt of an alarm message, the nurse may send an acknowledgment message acknowledging receipt of the alarm message. Once again, the rules, algorithms or instructions 25 operating on dispatching system 14 for this alarm condition processes the acknowledgment and determines if additional action needs to be taken. For example, if an acknowledgment message is not received within a predetermined time, the algorithm could instruct the pump 12 to issue a local alarm to alert those caring for the patient in the vicinity of the patient of this alarm condition. Of course, if the alarm condition is acknowledged before the predetermined time has expired 29, no such local alarm may be required as defined by the algorithm 25 and thus no local alarm will sound by pump 12.

In embodiments of patient care system 10 where an alarm condition has been forwarded to the dispatching system 14, it is desirable, but not required, to indicate on the pump 12 that an alarm occurred and that it has been forwarded. Further, in situations where the local alarm is suppressed, it is desirable, but not required, that the time remaining before the alarm sounds or is otherwise indicated locally on the pump 12 be displayed so that the clinician located in the vicinity of pump 12 may see and act upon this information appropriately.

Figure 4:
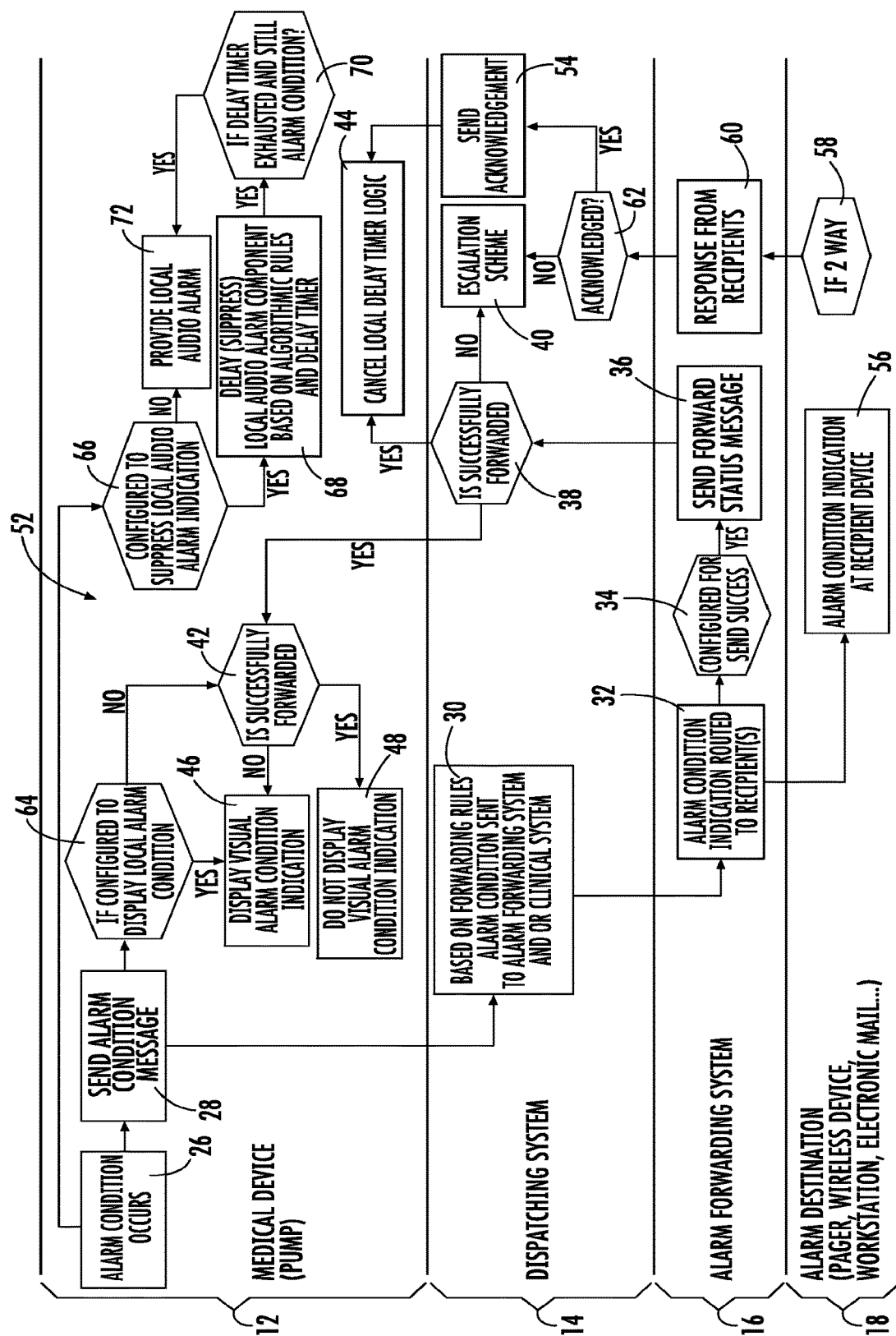
FIG. 4 is a flow chart of one embodiment of the patient care system of FIG. 1.

Further, a desirable function of the patient care system 10 is the capability to have confirmation that an alarm has been successfully delivered. As shown in FIGS. 3 and 4, the algorithm 25 running on dispatching system 14 could, if so defined, send a "successfully forwarded" message 31 back to the pump 12 after alarm messages have been sent to the appropriate personnel by the dispatching system 14 as described above. This "successfully forwarded" message 31 could be processed by the rules, algorithms or instructions 25 on dispatching system 14, alarm forwarding system 16 or pump 12 software and rules, algorithms or instructions to take action as defined by such software and rules, algorithms or instructions. For example, beyond just delivering such a "successfully forwarded" message 31 to the pump 12, the "successfully forwarded" message 31 may be displayed, including by activation of an audible, visual or tactile messaging systems as described herein to alert an appropriate caregiver of such receipt.

Each combination of alarm forwarding, acknowledgment, and particular kinds of suppression can be referred to as a suppression protocol. For example, the combination of suppressing a local auditory alarm until either a set time has elapsed or an alarm forwarding confirmation or acknowledgment was received is a first suppression protocol, while the combination of suppressing a remote alarm to a supervisor until either a set time has elapsed or a primary care giver cleared an alarm locally at the medical device is a second suppression protocol. Various suppression protocols can be created by hospital personnel via use of the rules editor mentioned previously, which can in one embodiment be incorporated into the Hospira MedNet™ software. The various suppression protocols can further be selectively applied by the care system based on the content of medical device data messages, alarm messages, and other information available to the system. As such, particularly stringent suppression protocols can be applied to low priority alarms automatically while more lax suppression protocols are applied to higher priority alarms.

In all of the above situations in which the content of a data message from pump 12 or the content of an alarm message were used to control the manner in which an alarm was generated, suppressed, or forwarded, the clinical care area (CCA) of the pump or medical device 12 can be used additionally or in the alternative as an input to a rule or can be used to select which rule should to be applied. This functionality provides significant benefits in that an alarm forwarding protocol or alarm suppression protocol might be appropriate for a given medical situation in one CCA and not appropriate in another. For example, the temporary interruption of a basic saline drip may be a low priority alarm towards which a stringent suppression protocol is applied in one CCA while the same medical event is a high priority in a level 4 NICU where the slightest divergence from a planned treatment can be more problematic for the patient. The CCA can be received as an input for any of these determinations by first being programmed into the medical device when it is deployed or provided in a drug library downloaded to the medical device, and subsequently selected by the clinician on the device so that the selected CCA information is delivered as part of the data message generated by the medical device 12. In the alternative, the CCA can be determined indirectly from the data message and/or alarm message by conducting a lookup operation on a database associated with a server that is in communication with a plurality of the medical devices in the healthcare facility. For example, an ID number associated with a pump could be received in a data message and then applied to a database to lookup the CCA area in which the pump had last been deployed, programmed in, or heard from via the network.

FIG. 4 shows the operation of one possible function of the patient care system 10. In this function, the dispatching system 14 and alarm forwarding system 16 are shown as separate systems. But, as described above, it is intended to be within the scope of the invention that the dispatching system 14 and alarm forwarding system 16 be combined into a single system or software module that performs the functions of the dispatching system 14 and alarm forwarding system 16 as described herein. Further, as can be seen in FIG. 4, the medical pump 12 itself may operate according to certain algorithms and may itself perform some of the functionality of the dispatching system 14 and alarm forwarding system 16.

In this example, if an alarm condition occurs at 26, the pump 12 generates an alarm condition message at 28. This alarm condition message is sent from pump 12 to the dispatching system 14 where the alarm condition message is evaluated at 30. The alarm condition message preferably includes information relevant to the alarm such as pump 12 ID, the patient ID/name, location of pump 12 and type/concentration/name of drug used. Pump 12 gets acknowledgement from the server of the dispatching system 14 that it received the alarm and acknowledgement from the forwarding system 16 and/or the alarm destination or recipient entity.

The evaluation at 30 occurs according to rules, algorithms or instructions established in the dispatching system 14. If, at step 30, it is determined that the alarm condition received from pump 12 should be passed to the alarm forwarding system 16 to be managed, the alarm condition is passed to the alarm forwarding system 16 where it is received at step 32. Alarm forwarding system 16 then forwards the alarm condition to the appropriate personnel via monitor/controlling systems 18 according to the rules, algorithms or instructions established in alarm forwarding system 16 for that particular alarm condition. Alarms have different priorities and repeat rates and require different responses. As a result, the rules, algorithms or instructions established in alarm forwarding system 16 determine which alarms get priority when one or more alarms are present at the same time as well as the appropriate routing, timing and display of alarm information in alarm conflicts. Further, the rules, algorithms or instructions established in alarm forwarding system 16 determine how, when and by whom alarms may be cancelled or suppressed, particularly in alarm conflict situations.

The monitor/controlling system 18 to which the alarm forwarding system 16 forwards the alarm condition may be any of a number of devices such as a pager, mobile phone, wireless device, tablet, workstation, email or any other form of communication that is able to communicate with the alarm forwarding system 16 and communicate information to the appropriate personnel. In the embodiment shown, the dispatching system 14 itself evaluates, according to rules, algorithms or instructions established in the dispatching system 14, whether the alarm condition received from pump 12 should be passed to the alarm forwarding system 16 to be managed. In an alternate embodiment, the dispatching system 14 contains no such evaluation system but instead passes the alarm message directly to the alarm forwarding system 16.

Upon receipt of an alarm condition message by the alarm forwarding system 16 at 32, in the embodiment shown, the program passes to step 34 where it is determined whether the alarm forwarding system 16 is configured to send a "successfully received" acknowledgment of the alarm condition message. If the alarm forwarding system 16 is so configured, the program passes from step 34 to step 36 where a "successfully received" acknowledgment message is generated and sent from the alarm forwarding system 16 to the dispatching system 14.

The "successfully received" message sent from alarm forwarding system 16 is received at the dispatching system 14 at step 38. Step 38 determines whether the alarm condition message originally generated by pump 12 and passed to dispatching system 14 was successfully forwarded to the alarm forwarding system 16. If, according to the logical operations of this step 38, the alarm condition message was not received by the alarm forwarding system 16, the program passes to step 40 where an escalation scheme is entered. The escalation scheme includes a determination, by rules, algorithms or instructions, of the appropriate response when an alarm condition message has not been acknowledged. Examples of such an appropriate response could be resending the alarm condition message, sending the alarm condition message to another monitor/controlling system 18, triggering a local display of the alarm condition on the pump 12, causing the display of an alarm alert condition at some other device, or any other appropriate response as determined by those having care of the patient and which have been programmed into the rules, algorithms or instructions operating on the dispatching system 14.

If the alarm condition message generated by pump 12 was ultimately received by the alarm forwarding system 16, then at step 38 a confirmation message is automatically sent to both steps 42 and 44 which are processed on the pump 12 by the operation of the logic 52 as explained above. At step 42, whether the alarm condition message was successfully forwarded to alarm forwarding system 16 is evaluated. If the alarm condition message was not successfully forwarded to the alarm forwarding system 16, the program passes to step 46 where a local alarm is visually displayed. If however, it is ascertained at step 42 that the alarm condition was successfully received by the alarm forwarding system 16, the program passes to step 48 where no local alarm is displayed by pump 12.

In this embodiment, pump 12 includes a local delay timer 50 as described above. Such a local delay timer 50 is activated when an alarm condition message is sent at step 28 by the pump 12 to the dispatching system 14. As mentioned, at step 38 the dispatching system 14 determines whether the alarm condition message generated by pump 12 was received by the alarm forwarding system 16. If the alarm condition message was ultimately received by the alarm forwarding system 16, the program also passes to step 44. Step 44 determines whether to cause the local delay timer 50 to cease. This determination at step 44 occurs according to rules, algorithms or instructions. In particular, this determination preferably takes into consideration whether an acknowledgment of receipt of an alarm message 54 has been sent by medical personnel at 58 and ultimately passed through steps 60 and 62 to step 54 where an acknowledgment message is sent from step 54 to step 44. Logic 52 (FIG. 1 or general arrow in FIG. 4) within pump 12 is set up to send a local alarm message if the local delay timer 50 (FIG. 1) exceeds its allotted time and preferably under the rules, algorithms and rules governing step 44, where no acknowledgment of an alarm condition message is received from the dispatching system 14 via step 54. However, upon receipt of an acknowledgement of an alarm condition message from the dispatching system 14 at 54, the local delay timer 50 ceases counting and no local alarm message is generated. The length of the delay set in the local delay timer 50 can be set, for example, according to the priority of the type of alarm 28 generated or the type/concentration/name of drug being infused by the pump 12. Further, if receipt of an acknowledgement of an alarm condition message arrives from step 54 after the timeout of the local delay timer 50, and as a result a local alarm has already started, according to rules, algorithms or instructions, the patient care system 10 can stop the local alarm, restart the local delay timer 50 or both.

Receipt at the monitor/controlling system 18 of an alarm condition causes the monitor/controlling system 18 to display the alarm condition at 56. This display may take the form of visual, audible or tactile displays. For example, the display may cause an audible alarm to sound indicating to the clinician the receipt of an alarm condition message. Further, the display may, on a viewing screen, display information related to the alarm condition message. In addition, the display may include activation of a visual indicator of the receipt of an alarm condition message such as a flashing light. Finally, the display may take the form of a tactile display such as a vibrating device indicating to the clinician the receipt of an alarm condition message. This list of possible displays is intended to illustrate possible displays or indications that a monitor/controlling system 18 may use. However, it is to be understood that this list is illustrative and not intended to be limiting. As a result, it is intended that any type of display that attracts the attention of the clinician to the receipt of an alarm condition message or displays or otherwise communicates the contents of an alarm condition message is intended to be within the scope of the present patient care system 10.

Upon receipt of an alarm condition message by a monitor/controlling system 18, the clinician may send an "acknowledgment of receipt" message back to the dispatching system 14 if their destination device permits two-way communication. Generating and sending such an acknowledgment message occurs at the monitor/controlling system 18 at 58. The acknowledgment receipt message is sent from the monitor/controlling system 18 to the alarm forwarding system 16 at 60 where the acknowledgment of the receipt of the alarm condition message is passed to the dispatching system 14 at 62. Step 62 determines whether the alarm message 28 previously sent from the dispatching system 14 has been acknowledged. If it has not, the program passes to 40 where an escalation scheme is determined according to rules, algorithms or instructions.

If, at step 62, it has been determined that an alarm condition acknowledgment message has been received, the program passes to step 54 where acknowledgment message is sent from the dispatching system 14 to the pump 12 at 44. This alarm condition 28 is evaluated at 64 to determine, according to rules, algorithms or instructions, if this alarm condition requires the display of a local alarm on pump 12. Whether such an alarm condition 28 requires the display of a local alarm on pump 12 is determined according to certain rules, algorithms or instructions that have been programmed into the pump 12. If the alarm condition 28 requires that a local alarm be displayed on pump 12, such an alarm is displayed at 46. If the alarm condition 28 does not require that a local alarm be displayed, the program advances to 42 where it is evaluated whether the alarm condition was successfully forwarded to appropriate personnel through the dispatching system 14 and alarm forwarding system 16.

The creation of an alarm condition at 26, in addition to the sending of an alarm condition message at step 28, also causes the program operating according to the logic 52 on pump 12 to move to step 66 where it is determined, according to rules, algorithms or instructions, whether pump 12 is configured to suppress the local alarm audio alarm. Determining whether pump 12 is configured to express the local alarm audio alarm is done according to rules, algorithms or instructions programmed on the pump 12.

If, at step 66, it is determined, according to rules, algorithms or instructions, that the pump 12 is configured to suppress the local audio alarm, the program advances to step 68 where it is evaluated whether to delay or suppress the local audio alarm based on its rules, algorithms or instructions including, but not limited to, reference to the current stage of the local delay timer 50. If, at step 68, it is determined that the local audio alarm should be suppressed, the program passes to step 70. Step 70 determines whether the local delay timer 50 has exhausted its predetermined delay time and the alarm condition still persists. If the local delay timer 50 has exhausted its local delay time and the alarm condition still persists, the program passes to step 72 where pump 12 provides a local audio alarm even though the alarm had previously been determined to be suppressed. The reason the alarm suppression is overridden in this embodiment is that the failure to receive an acknowledgment of receipt of an alarm notice, as evidenced by the local delay time 50 timing out, has been determined, according to rules, algorithms or instructions, to require an alarm to be generated. Also, according to rules, algorithms or instructions, the alarm can be generated immediately or can be generated after taking further action (e.g., resending the alarm message to see if an acknowledgment or receipt of the alarm message returns). If at step 66 it is determined that pump 12 is not configured to suppress a local audio alarm indication, the program passes to step 72 where pump 12 provides a local audio alarm. Either or both a local audio or visual alarm can be produced at 46 and 72.

Although embodiments of the patient care system 10 discussed above had the alarm forwarding system 16 sending a "successfully received" acknowledgment of the alarm condition message, this is not required for the patient care system 10. Further, although those embodiments of the patient care system 10 had an escalation scheme 40, that also is not required for the patient care system 10. Similarly, various explicit acts, evaluations, messages sent or suppressed, alarms activated or suppressed and similar aspect of the embodiment described above and with respect to other embodiments shown may be eliminated or added in a wide variety of permutations and combinations and still fall within the scope of the invention. Patient care system 10 allows for the management of alarms in all varieties of the term "management." The various aspects of "managing" alarms given in this description are intended to be illustrative and not limiting.

Figure 5:
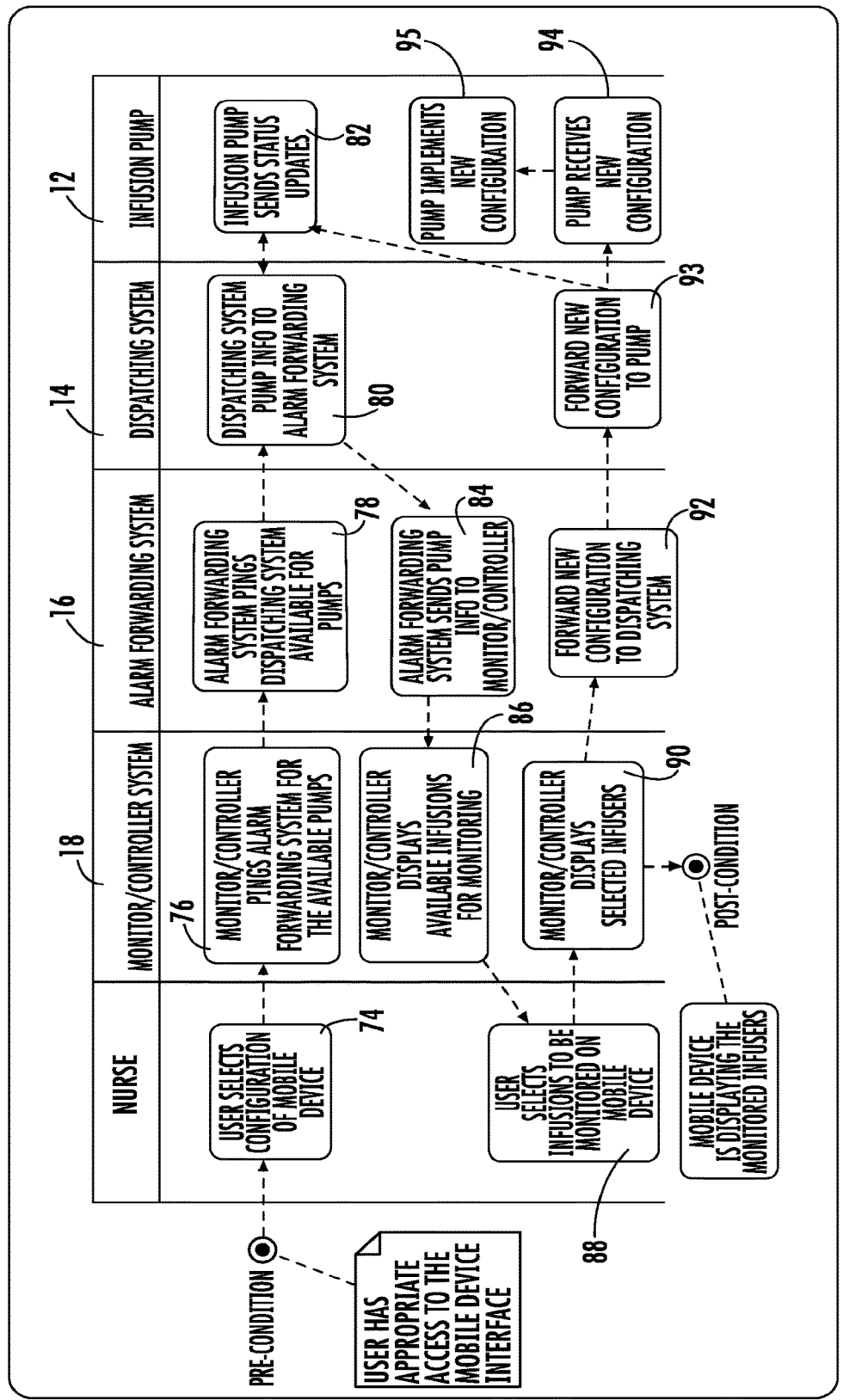
FIG. 5 is a chart of one embodiment of patient care system showing the process of configuring a pump from a monitor/controlling system.

FIG. 5 indicates the interrelationship between an administrator, such as an information technology (IT) specialist, a biomedical engineer, or a nurse or other clinician with responsibility for care of a patient, with the pump 12 through dispatching system 14, alarm forwarding system 16, and monitor/controlling system 18. Where the administrator desires to configure the pump 12 at 74, the administrator sends a command through the monitor/controller system 18 at 76.

Where an administrator desires to reconfigure a pump 12, the monitor/controller system 18 "pings" the alarm forwarding system 16 at 78 to determine which pumps 12 are available for configuration. The alarm forwarding system 16 then "pings" the dispatching system 14 at 80 to determine which pumps 12 are available for configuration. The pumps 12 in communication with dispatching system 14 send their identification information and data to dispatching system 14 at 82. This can be a near real time push of data from the pumps 12 to the dispatching system 14 or the data can be pulled in response to a request or "ping" of the pumps by the dispatching system 14. Dispatching system 14 then sends information about the available pumps 12 to the alarm forwarding system 16 10 at 84 where such information is sent to the monitor/controller system 18 at 86 where the monitor/controller 18 displays the relevant information about this particular pump 12 including the current status of the pump and the range of available options for reconfiguration. By monitor/controlling system 18 displaying this information, the information is made available to the administrator.

Once the administrator has determined which pumps 12 are available for configuration, the administrator selects the pump 12 to be configured at 88. The administrator makes the desired selection on the monitor/controller system 18 which then displays the newly configured settings about this particular pump 12 at 90. Once the administrator has entered the particular parameters for configuration of the desired pump 12 on the monitor/controlling system 18, the monitor/controller system 18 passes this information to the alarm forwarding system 16 at 92 which sends the information to the dispatching system 14 at 93 where the parameters configuration are sent to the selected pump 12 by the dispatching system 14 where they are received by the pump 12 at 94 and implemented on the pump 12 at 95.

A similar process is employed for the administrator to configure the dispatching system 14, alarm forwarding system 16 or the monitor/controller system 18 itself. If the monitor/controller system 18 itself is to be configured, the configuration can take place directly by entering the new configurations on the monitor/controlling system 18. However, it may be desirable to alert others through the dispatching system 14 or clinical system 24 of such configuration changes. In that case, the monitor/controller system 18 sends the configuration information to the alarm forwarding system 16 which sends this information to the dispatching system 14 which then sends the information, according to rules, algorithms or instructions on the dispatching system 14, to the appropriate locations.

Where the alarm forwarding system 16 is to receive new configurations, configurable aspects of the alarm forwarding system 16 are displayed on the monitor/controller system 18. The desired configurations for the alarm forwarding system 16 are entered into the monitor/controlling system 18 which then sends the new configurations to the alarm forwarding system 16 to be implemented. Again, it may be desirable to alert others through the dispatching system 14 or clinical system 24 of such configuration changes. In that case, the alarm forwarding system 16 sends the configuration information to the dispatching system 14 which then sends the information, according to rules, algorithms or instructions on the dispatching system 14, to the appropriate locations.

Where the dispatching system 14 is to receive new configurations, configurable aspects of the dispatching system 14 and alarm forwarding system 16 are received from the dispatching system 14, passed through the alarm forwarding system and displayed on the monitor/controller system 18. The desired configurations for the dispatching system 14 are entered into the monitor/controlling system 18 which then sends the new configurations to be implemented by the dispatching system 14. Again, it may be desirable to alert others through the dispatching system 14 or clinical system 24 of such configuration changes. In that case, the dispatching system 14 sends the information, according to rules, algorithms or instructions on the dispatching system 14, to the appropriate locations.

In this embodiment, the interface 22 and clinical system 24 are not explicitly shown. However, the interface 22 and clinical system 24 may be incorporated into a monitor/controller system 18. However, it is to be understood that interface 22 and clinical system 24 may be separate and independent systems or that the functions of interface 22 and clinical system 24, in whole or in part, may be performed by the dispatching system 14, alarm forwarding system 16 or monitor/controlling system 18. Further, it is within the scope of the patient care system 10 that the function or elements or both of the dispatching system 14, alarm forwarding system 16, interface 22, clinical system 14 and monitor/controlling system 18 be combined in any permutation or combination of such functions or elements including into a single system.

Figure 6:
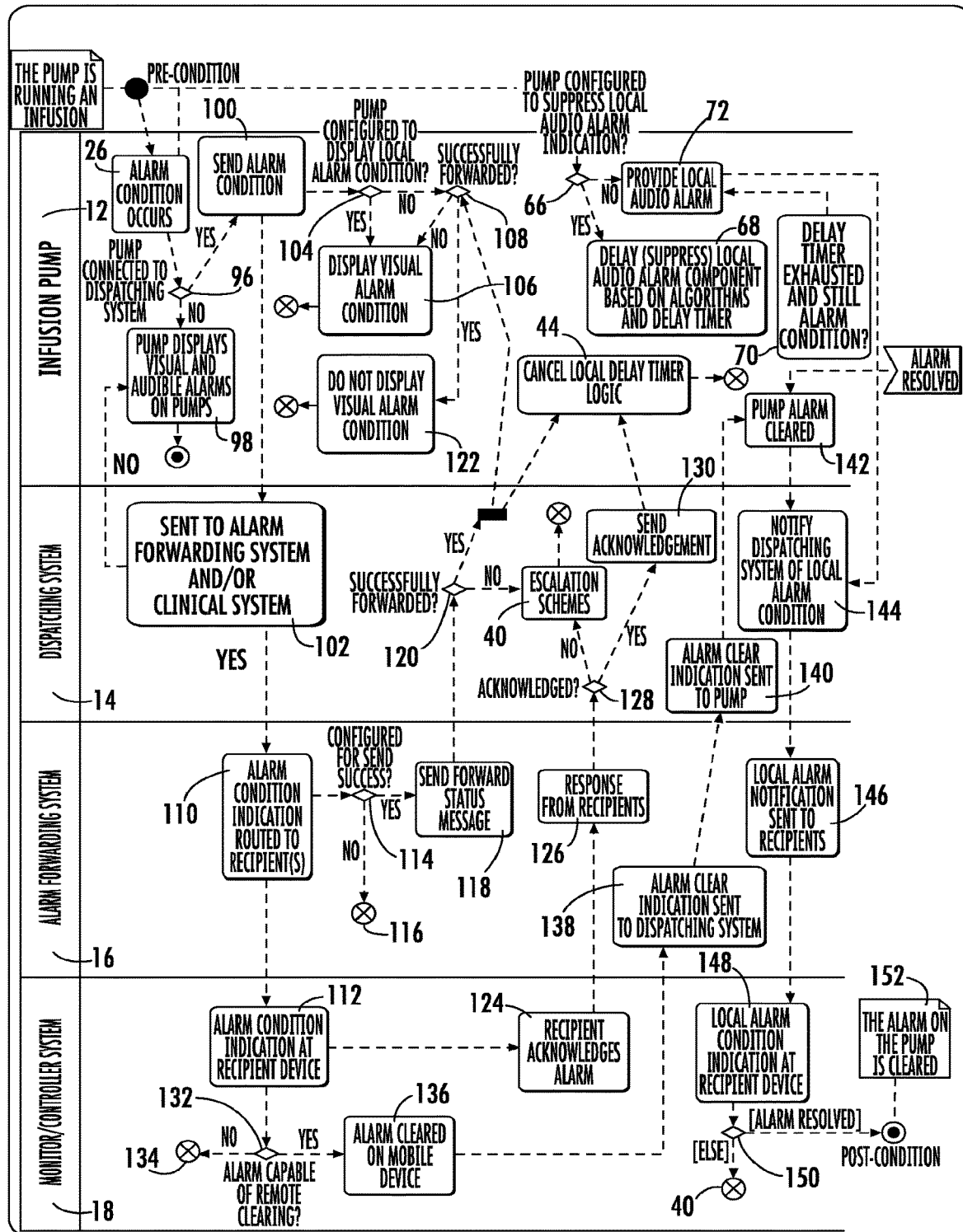
FIG. 6 is a flow chart of one embodiment of patient care system showing the alarm forwarding and acknowledgment functions.

The operation of the patient care system 10 with respect to the alarm forwarding function is shown in FIG. 6. When an alarm condition occurs at 26, pump 12 determines at 96 whether pump 12 is connected to the dispatching system 14. If pump 12 is not connected to the dispatching system 14, the program passes to step 98 where the pump displays a visual or audible alarm or both on pump 12 indicating that pump 12 is not connected to the dispatching system 14. If, at step 96, it is determined that the pump 12 is connected to the dispatching system 14, the program passes to step 100. At step 100, pump 12 sends an alarm condition notice to the dispatching system 14 where the dispatching system 14 receives the alarm condition notice at 102. In addition to sending an alarm condition notice to the dispatching system 14, the program passes from step 100 to step 104 where it is determined whether the pump 12 is configured to display a local alarm condition indicating that pump 12 is not connected to the dispatching system 14. If pump 12 is configured to display such a local alarm notice, the program passes to step 106 where such an alarm condition is displayed or otherwise indicated. If pump 12 is not configured to display such an alarm notice, the program passes to step 108 where action occurs, as will be discussed hereafter.

As mentioned above, when an alarm condition is generated at 26 and the pump 12 is connected to the dispatching system 14, an alarm condition message is sent at step 100 to the dispatching system 14 where it is received at step 102. At step 102, the alarm condition message is evaluated according to the rules, algorithms or instructions that determine whether the alarm condition message should be forwarded to the alarm forwarding system 16 or the monitor/controller system 18 or both. If, at step 102, it is determined that the alarm condition message should not be forwarded to either the alarm forwarding system 16 or monitor/controller system 18, the program passes to step 98 where the pump 12 will display or generate an alarm on the pump 12.

If, at step 102, it is determined that the alarm condition message should be forwarded to either the alarm forwarding system 16 or monitor/controller system 18, the program passes to step 110 in the alarm forwarding system 16. At step 110, the program determines, according to rules, algorithms or instructions, whether the alarm condition should be routed to a recipient and if so, which recipient. If it is determined that the alarm condition notice should be forwarded to a recipient, the program passes from step 110 in the alarm forwarding system 16 to step 112 in the monitor/controller system 18. In order for the program to reach step 110, an alarm condition message must have been received by the alarm forwarding system 16. Consequently, at step 110, the program passes to step 114 where it is determined whether the alarm forwarding system 16 is configured to send acknowledgment of a successful receipt of an alarm notice message. If the alarm forwarding system 16 is not configured to send such an acknowledgment, the program passes to 116 were no further action is taken. However, if the alarm forwarding system 16 is configured to send such an acknowledgement, the program passes to step 118 where such acknowledgment is generated by the alarm forwarding system 16 and sent to the dispatching system 14 to be received at step 120. If, at step 120, it is determined that the alarm condition message was successfully received by the alarm forwarding system 16, the program passes to step 108 in the pump 12.

If, at step 108, it is determined that the alarm condition message generated at step 100 was not received by the alarm forwarding system 16, the program passes to step 106 where an alarm condition indicating that the alarm condition message was not received by the alarm forwarding system 16 is displayed on the pump 12. If however, at step 108, it is determined that the alarm condition message generated step 100 was successfully received by the alarm forwarding system 16, the program passes to step 122 where no alarm is displayed locally on pump 12.

If, at step 120, it is determined that the alarm condition message received from pump 12 by the dispatching system 14 at step 102 has not been successfully forwarded to the alarm forwarding system 16, the program passes to an escalation scheme 40 where the appropriate level of escalation is determined according to rules, algorithms or instructions as discussed above. Also at step 120, if it is been determined that the alarm condition message generated by pump 12 and received by dispatching system 14 has also been successfully received by the alarm forwarding system 16, the program also passes to step 44 where the local delay timer 50 is canceled and no alarm message is generated.

If, in the monitor/controller system 18 at step 112, an alarm condition indication is indicated on a monitor/controlling system 18, the program passes to step 124 where the recipient of the alarm condition message is given the opportunity to acknowledge receipt of the alarm condition message. If the recipient chooses to generate an acknowledgment of the receipt of such a message, the program passes to step 126 in the alarm forwarding system 16 where the acknowledgement is passed to step 128 in the dispatching system 14. Step 128 ascertains whether the recipient has acknowledged receipt of the alarm condition message sent by pump 12. If the answer is yes, the program passes to step 130 where acknowledgment to send from the dispatching system 14 to step 44 where the local delay timer 50 is canceled and no alarm message is thus generated.

If an alarm condition indication is sent to a monitor/controlling system 18 at step 112, the program passes to step 132 where, according to rules, algorithms or instructions, it is ascertained whether the alarm condition is capable of remote clearing. If the alarm condition is not capable of remote clearing, the program passes to step 134 where no further action is taken. However, if the alarm condition is capable of remote clearing, the program passes to step 136 where the alarm may be cleared on the monitor/controlling system 18 by a qualified clinician.

The program then passes to step 138 in the alarm forwarding system 16. Step 138 passes the alarm clearing message to step 140 of the dispatching system 14 which passes the alarm clearing message to pump 12 at step 142. At step 142, the pump alarm is cleared on pump 12. If the pump alarm is cleared at step 142 on pump 12, the program passes to step 144 of the dispatching system 14. At step 144 the dispatching system 14 is notified that the alarm condition message previously generated by pump 12 at step 100 has been cleared remotely. The program then passes to step 146 on the alarm forwarding system 16 where a local alarm notification is sent to the appropriate recipients as determined by the rules, algorithms or instructions running on alarm forming system 16. Further, the program passes to step 148 in the monitor/controller system 18 where a local alarm condition is indicated on the appropriate monitor/controlling systems 18 indicating that an alarm condition notice has been cleared.

The program then passes to step 150 where it is determined whether the alarm condition has been resolved. If the alarm condition has been resolved, the program passes to step 152 on pump 12 where the alarm on pump 12 is cleared. If the program determined at step 150 that the alarm condition is not been resolved, the program passes to step 40 where an escalation scheme is entered into so that the appropriate action, according to the rules, algorithms or instructions previously determined, can be taken to resolve the alarm condition issue. At step 144, the program also passes to step 72 where, as described above, if the pump 12 is not configured to suppress a local edible alarm, pump 12 will provide a local audible alarm.

When an alarm gets cleared, either manually by a clinician or automatically according to the rules, algorithms or instructions running on the patient care system 10, a "clearing alarm message" may be sent to all the entities that received the original alarm. Such clearing alarm message may indicate how the alarm was cleared, when, and by whom and may include an indication of what the original alarm was, its timestamp and how the alarm was resolved. Further, although the alarm has been shown as being cleared in certain locations, the alarm may be cleared from wherever a clinician has access to the patient care system 10, whether at the pump 12, dispatching system 14, alarm forwarding system 16, clinical system server 24 or monitor/controlling system 18. It may be desirable to explicitly indicate or highlight on the pump 12 itself that the clearing took place remotely in order to alert the nearby attending personnel of the source of the clearing. In addition, if the alarm is locally cleared before it was cleared remotely, the dispatching system server 14 will receive notice of this occurrence and forward such notice to the remote recipients.

Further, it is desirable if the alarm is cleared remotely but not locally, that the local delay timer described above be employed to re-start the alarm sequence described herein after the expiration of a predetermined time in case a clinician clears the alarm remotely but forgets to check on the pump 12 and clear the alarm locally on the pump.

Figure 7:
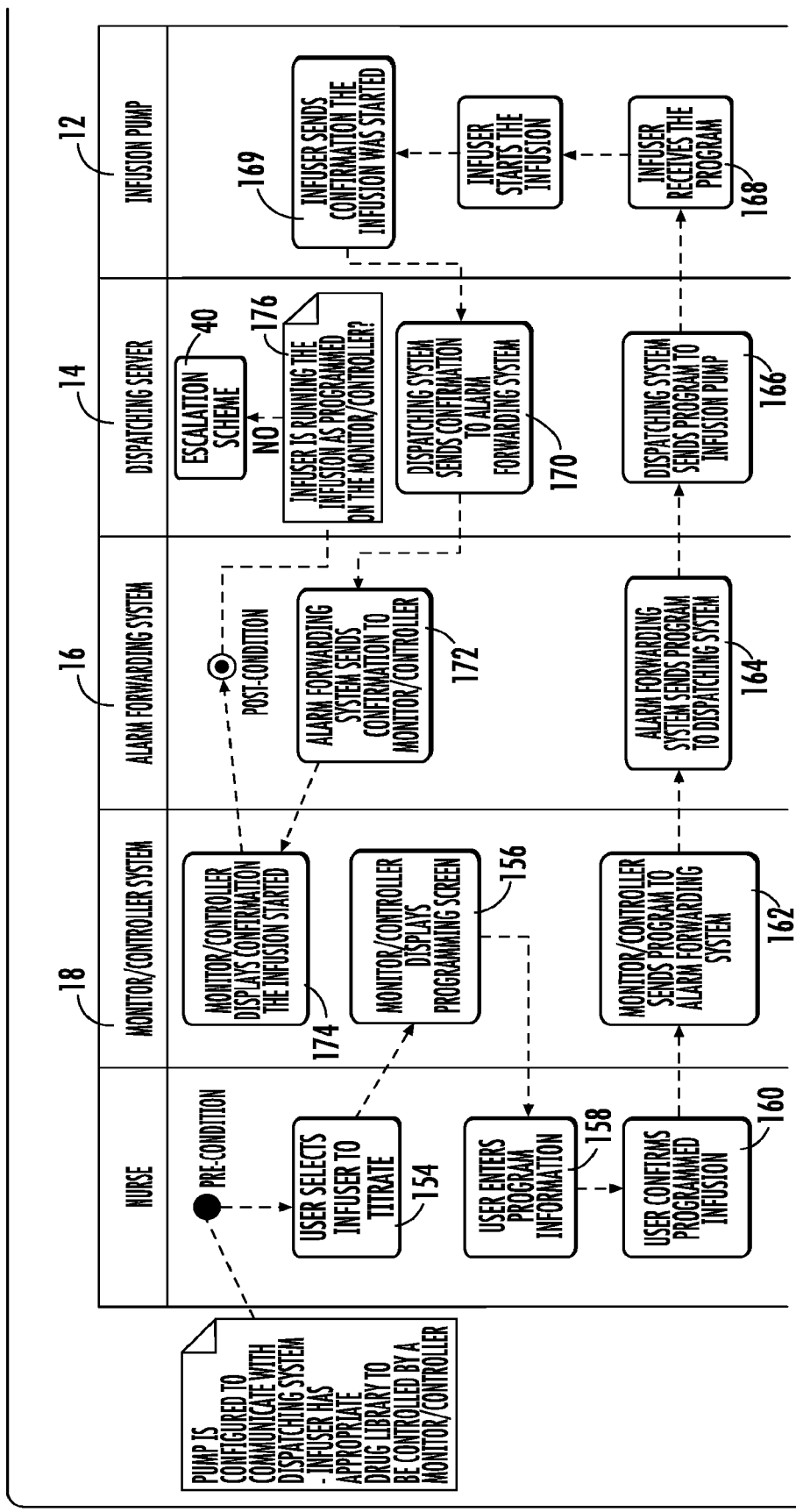
FIG. 7 is a chart of one embodiment of the patient care system showing the process of changing the pump infusion program with a monitor/controlling system.

FIG. 7 illustrates an embodiment of the patient care system 10 where the infusion program operating on pump 12 is modified or replaced by an operator. In this embodiment of the patient care system 10, the pump 12 must be connected to the dispatching system 14 in order to be controlled by the monitor/controller system 18 as will be described hereafter. Further, the pump 12 must have an appropriate drug library with settings selected or configured by the manufacturer or more preferably the healthcare facility that allow the infusion program to be modified or replaced remotely from a monitor/controlling system for alarm management purposes. The drug library must be stored on the pump or otherwise be accessible to the pump 12. In this embodiment, an appropriate or authorized person, for example a nurse providing care to a patient, on their respective monitor/controller system 18 selects some aspect of the operation of the pump 12 with respect to the patient. For example, as shown in FIG. 7, at step 154, the clinician could select the infusion titrate. Consequently, at 156 the clinician accesses a programming screen on the monitor/controller 18. The clinician, at step 158, then enters the desired programming information on the programming screen of the monitor/controlling system 18. Thereafter, the process passes to step 160 where the clinician confirms the program information. The process then passes to step 162 where the monitor/controller system 18 sends the new program information to the alarm forwarding system 16 where it is received at step 164. At step 164, the alarm forwarding system sends the programming instructions to the dispatching system 14 where it is received at step 166. At step 166, the dispatching system 14 sends the program instructions to the infusion pump 12 where it is received and incorporated into the pump 12 at step 168. The pump 12 may act on the new or modified program instructions immediately as shown in FIG. 7 or may proceed in a delayed manner after local or remote confirmation.

As can be seen in the description of the patient care system 10, there are certain steps that are performed as part of the logic, whether software or by discrete logic on the various components of the patient care system 10 and pump 12. But, there are also certain steps that are performed by the clinician that are not part of or performed by such logic. Where a process involving the patient care system 10 involves steps performed by the clinician but that are not performed by the patient care system 10, whether in embodiments including the pump 12 or monitor/controller 18, the process steps performed by the clinician are not part of the patient care system 10.

Also as shown in FIG. 7, at 169 pump 12 sends confirmation to the dispatching system 14 that infusion by the pump 12 to the patient has started. The dispatching system 14 at 170 receives confirmation that the infusion by pump 12 was started and passes this information to the alarm forwarding system 16 at 172. At step 172, the alarm forwarding system 16 sends confirmation that the pump 12 has started infusion to the monitor/controller 18 at 174. At step 174, the monitor/controller system 18 displays a confirmation that the infusion by the pump 12 has started. At step 174, the monitor/controller system 18 displays that the infusion has started by the pump 12. This confirmation is also sent from the monitor/controller 18 to the dispatching system 14 at step 176 (via the alarm forwarding system 16). At step 176 the dispatching system 14 ascertains whether the infusion started by pump 12 is the desired infusion as programmed by the monitor/controller 18. If the infusion is not correct, the dispatching system 14 passes to step 40 where an escalation scheme is entered into and action taken according to the rules, algorithms or instructions set up in the escalation scheme.

Figure 8:
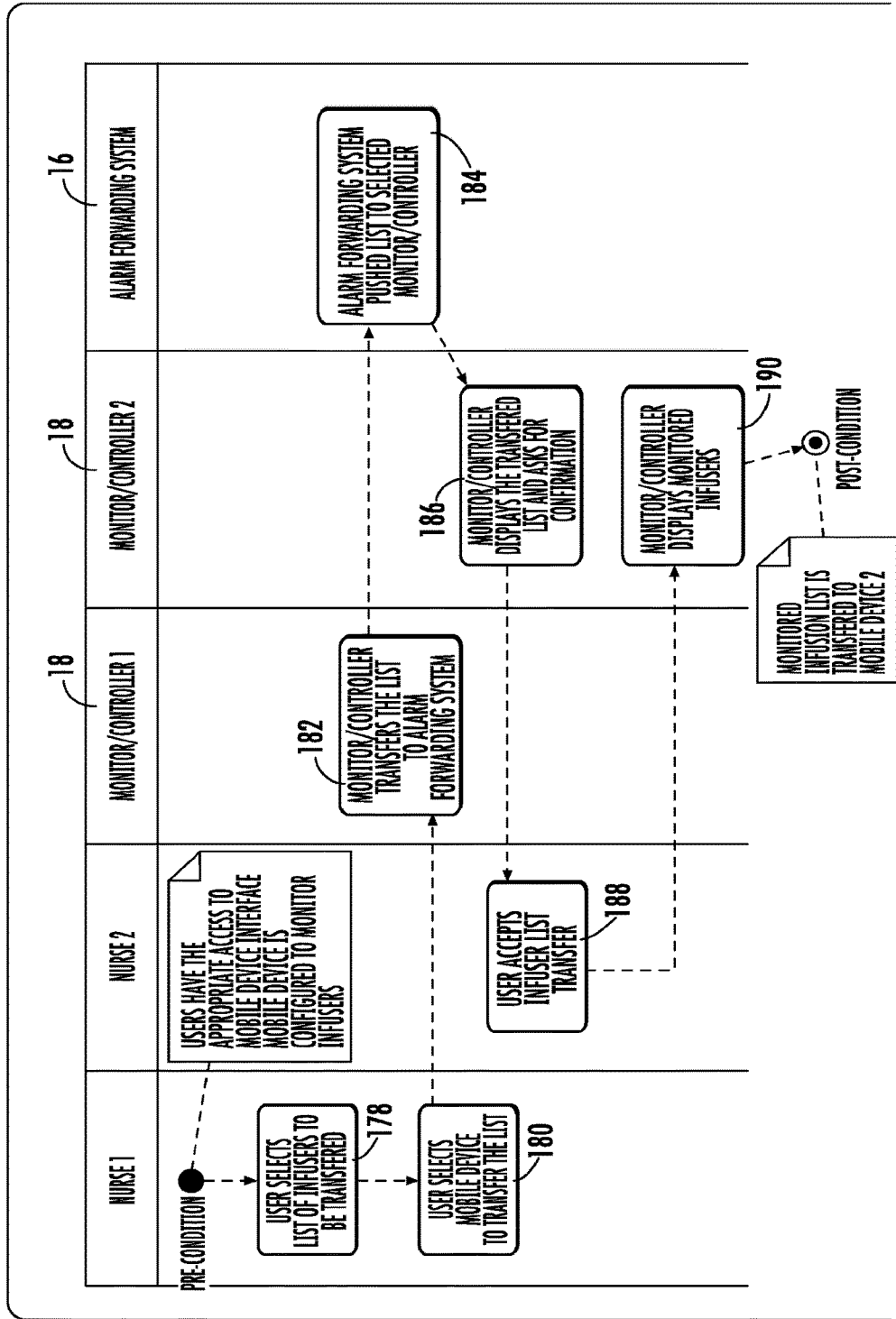
FIG. 8 is a chart of one embodiment of the patient care system showing the process of transferring oversight of one or more pumps from one monitor/controller system to another monitor/controlling system.

Another management function of the patient care system 10 is shown in FIG. 8. In this function, a clinician transfers responsibility for one or more pumps 12 to another clinician. To access this functionality, both the clinician doing the transferring and the clinician receiving the transfer of responsibility for the pumps 12 must have appropriate access to the dispatching system 14 and alarm forwarding system 16, for example, through each clinician's respective monitor/controlling systems 18 with their appropriate interfaces. By accessing the monitor/controller system 18, at 178 the clinician selects a list of pumps 12 to be transferred. The process passes to step 180 where the clinician selects the monitor/controlling system 18 to which the responsibility for the pumps 12 will be transferred.

The process passes to step 182 where the monitor/controller 18 for the person passing responsibility for the pumps 12 then transfers the list of selected pumps 12 to the monitor/controlling system 18 of the person receiving responsibility for the pumps 12 via the alarm forwarding system 16 where this information is received at 184. At step 184, the alarm forwarding system 16 pushes the list of selected pumps to the selected monitor/controller 18 receiving responsibility for the pumps 12 at 186. At 186, the respective monitor/controlling system 18 displays the transferred list of pumps 12 and ask for confirmation of the transfer. The clinician associated with the new responsibility for the pumps 12 then, on their monitor/controlling system 18, accepts the pump list transfer at 188. Also, as a result of the clinician accepting the pump 12 transfer list, the monitor/controller 18 of that clinician then displays the list of newly acquired pumps 12 at 190.

Figure 9:
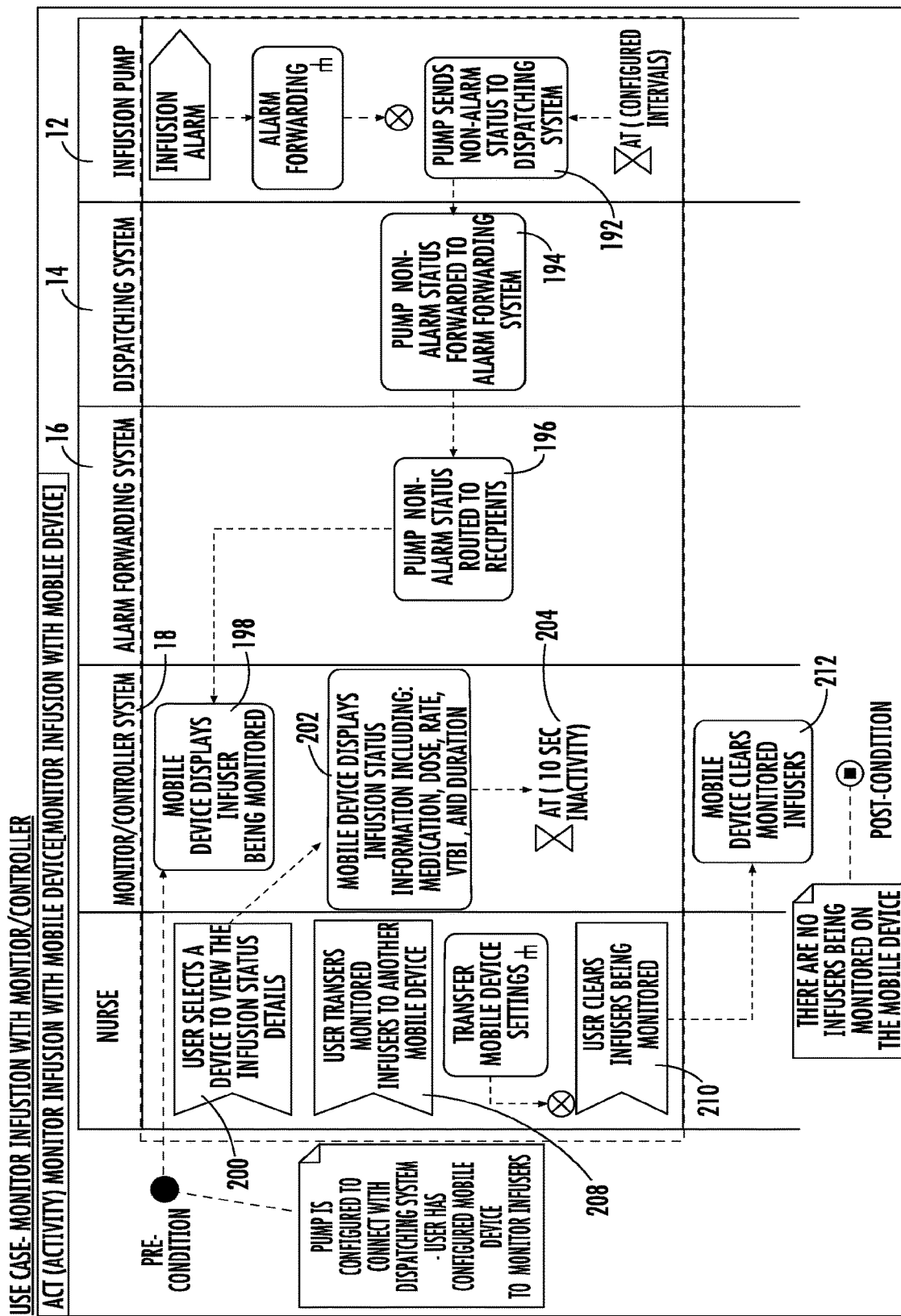
FIG. 9 is a chart of one embodiment of the patient care system showing the process of monitoring the infusion by a pump with a monitor/controlling system.

A monitor infusion function of the patient care system 10 is displayed in FIG. 9. Pump 12 is configured to interact with the dispatching system 14. At 192, pump 12 sends non-alarm status information to the dispatching system 14 where it is received at 194. Examples of such non-alarm status information include, but are not limited to, the medication being delivered, the dose, rate, volume to be infused (VTBI) and duration of infusion. Step 194 forwards the non-alarm status information from pump 12 to the alarm forwarding system 16 where it is received at 196. Step 196 then routes the pump 12 non-alarm status information to the appropriate recipient or recipients as configured by rules, algorithms or instructions operating on the alarm forwarding system 16. Each recipient of the pump 12 non-alarm status information receives this status information at step 198 on their respective monitor/controller system 18. As a result, the monitor/controller system 18 displays the non-alarm status information from pump 12 so that the clinician can be apprised of such status. If a particular clinician's monitor/controlling system 18 is monitoring more than one pump 12, it can be set to select and display individual information about each pump 12. At step 200, the clinician selects a pump 12 to view that pump 12's non-alarm status details. As a result of selecting a particular pump 12 to monitor, the monitor/controller system 18 at 202 displays the non-alarm infusion status information for that pump 12.

The patient care system 10 may also include functionality that affects the duration that certain information is displayed on the monitor/controller system 18. An example of such functionality is shown in FIG. 9. From 202, the program may pass to step 204 which is a timer that times the amount of inactivity associated with the clinician's interaction with the monitor/controller system 18. If a sufficiently long amount of time elapses according to rules, algorithms or instructions without the clinician interacting with the monitor/controller system 18 (e.g., 10 seconds), the program passes to step 206 where the monitor/controlling system 18 closes the detailed view of the non-alarm status information provided by a particular pump 12. Of course, the amount of time that must pass before activating this closing of the detailed view can vary and may be selectable by the clinician to suit the clinician's preference or may be preset according to certain safety protocols. Further, this functionality includes, in addition to the length of time certain information is displayed, also determining what information is displayed and for both, may take into consideration who the clinician is, what the pump status is and the location of the clinician.

As a result of having transferred responsibility for one or more pumps 12 to another monitor/controlling system 18, the clinician may clear their monitor/controlling system 18 of the transferred pumps 12. Of course, the clinician must first have transferred responsibility for the pumps 12 as is done at step 208 where the process described above is summarized into a single step 208. Thereafter, the program passes to 210 where the clinician clears the pumps 12 that have been transferred. The program then passes to step 212 where the monitor/controlling system 18 clears the previously monitored pumps 12 which have now been transferred to another clinician.

Figure 10:
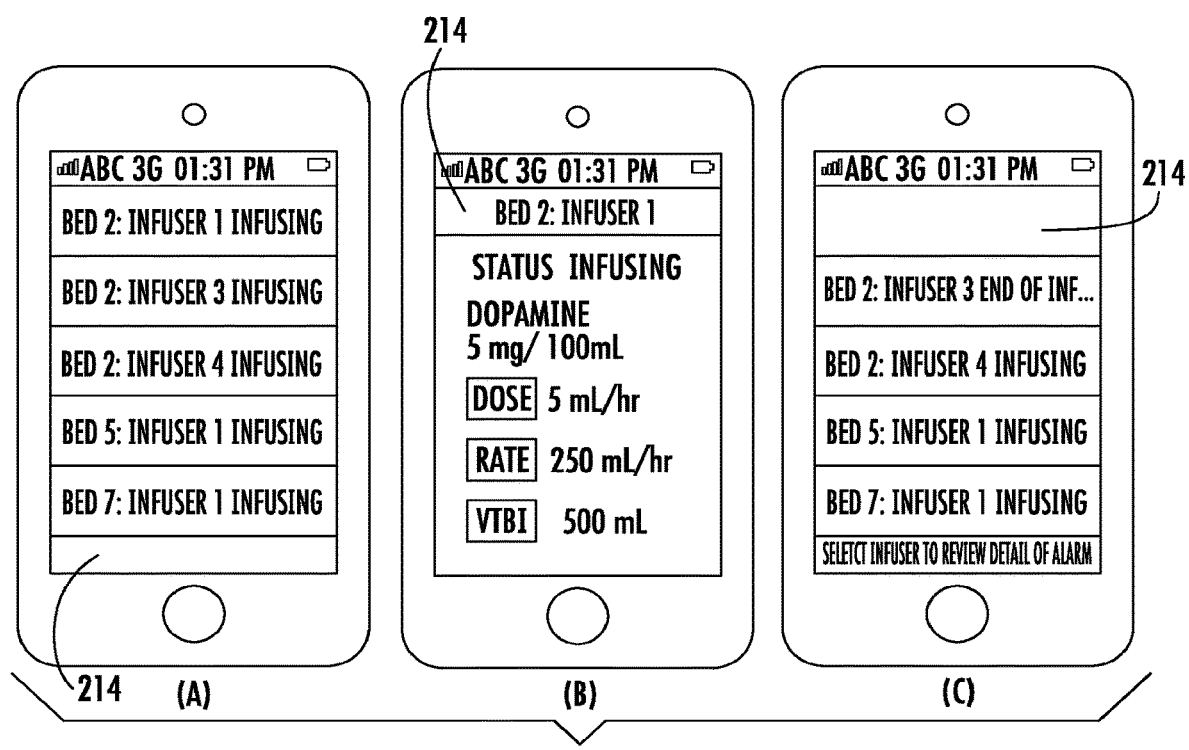
FIG. 10 is a top view of one embodiment of a monitor/controlling system user interface design in various states during operation.

FIG. 10 shows examples of the monitor/controlling system 18. Monitor/controlling system 18 may be a mobile phone, laptop computer, tablet or any other mobile device capable of interacting with the alarm forwarding system 16 and dispatching system 14, displaying information and allowing information to be entered and sent to the alarm forwarding system 16 and dispatching system 14. As can be seen in part A of FIG. 10, the status of devices being monitored located in several different locations (e.g., Bed 2, Bed 5 and Bed 7) can be displayed on a main status screen 214. The information displayed on the screen is the name of the pump 12 and the infusion status. Further as shown in part B of FIG. 10, the details of the infusion taking place by any particular pump 12 can be displayed once a pump 12 from the main status screen 214 is selected. For example, as can be seen in the example of part B of FIG. 10, where pump 12 is indicated as "Infuser 1" that is located at "Bed 2," the status "Infusing" is indicated as well as the drug being infused, in this case "Dopamine." Furthermore, the concentration of dopamine is indicated (5 mg/100 ml) as well as the dose (5 ml/hr), rate 10 (250 ml/hr) and VTBI (500 ml). A "patient" designation can of course be substituted for a "bed" designation without departing from the scope of the invention.

As shown in part C of FIG. 10, an alarm state can also be shown on the monitor/controller system 18. In this case, the pump 12 indicated as "Infuser 3" located at "Bed 2" is reaching the end of its infusion program. As a result, an "End of Infusion" 15 alarm message has been generated. One possible result of generating such an alarm message is that the monitor/controlling system 18 itself may indicate the alarm. In addition to indicating the status of particular pumps 12 (here, "End of Infusion"), the monitor/controlling system 18 may also activate a visual, audible or tactile alarm to alert the clinician of receipt of this alarm message.

Further, the order of display of the pumps 12 being monitored can be changed to represent the priority of their respective statuses. For example, as shown in part C of FIG. 10, the pump 12 designated "Infuser 3" at "Bed 2" is in a higher priority status than the other pumps 12 due to the presence of an alarm message associated with this particular pump 12. As a result, this pump 12 is listed higher on the display of the monitor/controlling system 18 than the other pumps 12 with lesser priority status in order to draw attention to this pump 12's heightened status.

Throughout this description, repeated mention has been made to "rules, algorithms or instructions." These rules, algorithms or instructions can be directed to virtually anything that is determined to be useful including, but not limited to, promoting safety or improving efficacy, longevity or ease of use. In addition, where the clinician is configuring or reconfiguring a pump 12, these rules, algorithms or instructions can include safeguards to warn clinicians if certain configurations are outside of accepted bounds or are dangerous so that the clinician may be required to confirm such configurations before they are accepted by the patient care system 10. Further, where, when and to whom alarm messages may be forwarded or communicated to may take into consideration the staff available, clinical care area (CCA), therapy being delivered, type of drug, condition of the patient, time of day, day of the week, whether there has been or is an alarm escalation scheme 40 in effect to name but a few possible considerations.

The patient care system 10 described herein, in one or more of the embodiments disclosed, has advantages over current systems in increased patient safety and increased ease of use for the clinicians. With respect to increased patient safety, the patient care system 10 in one or more embodiments increases patient safety by sounding an alarm when the alarm forwarding does not reach clinical personnel or they are unable to respond to or acknowledge the alarm in a timely manner. In this way, the possibility of a clinician missing or failing to respond to an alarm is decreased. The possibility of a clinician missing or failing to respond to an alarm is also decreased, and thus patient safety is increased, by creating alarm escalation procedures that help medical personnel back up each other in case an initial alarm is missed or failed to be responded to. Further, patient safety increases with one or more embodiments of the patient care system 10 because reaction time by medical personnel to adverse infusion events or pending adverse infusion events is reduced. This reaction time is reduced by alerting medical personnel to such adverse event or pending adverse event even though the medical personnel is physically distant from the pump 12.

Additionally, patient safety is increased in one or more embodiments of the patient care system 10 by creating a system of alarm evaluation and dispatch that operates according to rules, algorithms or instructions so that alarm management logic is removed from the individual and various monitor/controller systems 18 and corresponding communication technology and is instead governed and controlled by a reduced set (in some cases, a single set) of rules, algorithms and instructions operating on a smaller number of devices (in some cases, on a single dispatching system 14).

Further, patient safety is increased in one or more embodiments of the patient care system 10 by allowing medical personnel to program or modify an infusion without exposing the patient to unnecessary contact or the requirement that the pump 12 be programmed at the pump 12 itself. Because the clinician does not need to be physically present or come in contact directly with the pump 12, the likelihood of contamination of the patient by the clinician is reduced. In addition, because the clinician does not need to be physically present or contact the pump 12 directly, the likelihood of cross contamination by multiple clinicians is reduced when multiple clinicians utilize the same infusion pump 12. In this way, the pump 12 is not contaminated by a clinician in the first place and even if the pump 12 were initially contaminated, cross-contamination is eliminated because subsequent clinicians do not need to come in contact with or be in close proximity to the pump 12 to change or modify programming on pump 12 or check the status of the pump 12 or an infusion program running on pump 12. If necessary confirmations or double checks of program values previously done at the pump 12 can be done by the clinician on the monitor/controlling system 18.

In yet other embodiments of the patient care system 10, patient safety increases by reducing the chance of incorrect therapy delivery. The chance of delivering an incorrect therapy is reduced because the clinician need only become familiar with a single interface (monitor/controlling system 18) instead of needing to gain familiarity with the interfaces on a large number of devices which might be involved in therapy delivery. Further, the chance of delivering an incorrect therapy is reduced in one or more embodiments because there are checks built into the rules, algorithms or instructions implemented on the patient care system 10.

The patient care system 10 also increases ease of use for the clinicians. With respect to increasing ease of use, in one or more embodiments of the patient care system 10, patient care system 10 allows medical personnel to clear alarms remotely instead of requiring the personnel to move to the pump 12 to clear the alarm. Further, in one or more embodiments of the patient case system 10, ease of use for medical personnel is increased by reducing the time necessary and the difficulty involved in modifying or updating programming and infusion program updates. Besides producing a simplified process for modifying or updating such programming, ease of use is increased by requiring the clinician to become familiar with only a single interface (e.g., monitor/controlling system 18) instead of the interfaces for each device that might be involved in therapy delivery.

In addition, the patient care system 10, in one or more embodiments, increases ease of use for medical personnel by sending alarm messages to medical personnel even 5 when they are not in proximity of the device (i.e., they are outside of visual and acoustic range of the pump 12). Further, in one or more embodiments, information that is useful or needed by the medical personnel about an alarm message such as the pump 12 ID, pump 12 location, patient information, drug information, program information, etc. are provided with the alarm message to aid such personnel in evaluating the alarm. As a result, medical personnel can have greater range from their patients and still deliver safe and effective therapy.

Another aspect of the patient care system 10 that increases ease of use for medical personnel in one or more embodiments of the patient care system 10 is that alarm noise in the hospital is reduced, which is beneficial—especially at night time. The reduction in alarm noise is due to the processing of alarms according to rules, algorithms or instructions to eliminate false or unnecessary alarms thereby producing fewer audible or visual alarms. Reducing the number of annoying distracting, false or unnecessary alarms benefits not only the medical personnel but the patient and other nearby patients as well.

Not all of these advantages will be present in every embodiment of the patient care system 10; some embodiments may have only one of these advantages while other embodiments will have more than one advantage and some embodiments may have all of the advantages. The disclosure has been directed to certain embodiments, combinations, configurations and relative dimensions. It is to be understood, however, that the description given herein has been given for the purpose of explaining and illustrating the invention and are not intended to limit the scope of the invention. It is to be further understood that changes and modifications to the descriptions given herein will occur to those skilled in the art. Therefore, the scope of the invention should be limited only by the scope of the claims.

What is claimed is:

1. A system for reducing audible alarms generated at an infusion pump, the system comprising:
    a first computing system configured to interface with an infusion pump and connect over a network to a second computing system, the first computing system comprising one or more hardware processors configured to:
        receive an alarm condition generated by an infusion pump;
        transmit the alarm condition generated by the infusion pump to the second computing system over the network;
        delay, at the infusion pump, an audible alarm corresponding to the received alarm condition for a predetermined time period;
        display, at the infusion pump, a visual indication of the alarm condition;
        determine that the alarm condition is present after the predetermined time period has elapsed; and generate, at the infusion pump, the audible alarm based on the determination that the alarm condition is present after the predetermined time period has elapsed, wherein the second computing system is separate from the first computing system.

2. The system of claim 1, wherein the second computing system comprises one or more hardware processors configured to:

receive the alarm condition transmitted by the first computing system; and dispatch the alarm condition to one or more care provider computing systems, wherein the one or more hardware processors are further configured to receive an electronic message from the second computing system and cancel the alarm condition based on the received electronic message.

3. The system of claim 1, wherein the one or more hardware processors are further configured to transmit the alarm condition to a clinician computing device designated for the infusion pump.

4. The system of claim 3, wherein the one or more hardware processors are further configured to change the clinician computing device designated for the infusion pump to a secondary clinician device, thereby enabling the secondary clinician device to monitor the infusion pump.

5. The system of claim 3, wherein the clinician computing device is changed in response to a request for change.

6. The system of claim 3, wherein the clinician computing device is changed in response to escalation of the alarm condition.

7. The system of claim 1, wherein the delay is based on a clinical care area in which the infusion pump is located.

8. The system of claim 7, wherein the clinical care area is determined based on an identification data associated with the infusion pump.

9. The system of claim 1, wherein the one or more hardware processors are further configured to transmit the alarm condition to a third computing system different from the second computing system based on a determination that the transmission to the second computing system failed.

10. A method for reducing audible alarms generated at an infusion pump, the method comprising:

receiving, at a first computing system connected with an infusion pump, an alarm condition generated by an infusion pump;

transmitting the alarm condition generated by the infusion pump from the first computing system to a second computing system over a network;

delaying, at the infusion pump, an audible alarm corresponding to the received alarm condition for a predetermined time period after the transmission;

displaying, at the infusion pump, a visual indication of the alarm condition;

determining that the alarm condition is present after the predetermined time period has elapsed; and generating, at the infusion pump, the audible alarm based on the determination that the alarm condition is present after the predetermined time period has elapsed, wherein the first computing system is separate from the second computing system.

11. The method of claim 10, further comprising receiving an electronic message from the second computing system and canceling the alarm condition based on the received electronic message.

12. The method of claim 10, further comprising transmitting the alarm condition to a clinician computing device designated for the infusion pump.

13. The method of claim 12, further comprising changing the clinician computing device designated for the infusion pump to a secondary clinician device, thereby enabling the secondary clinician device to monitor the infusion pump.

14. The method of claim 12, wherein the clinician computing device is changed in response to a request for change.

15. The method of claim 12, wherein the clinician computing device is changed in response to escalation of the alarm condition.

16. The method of claim 10, wherein the delay is based on a clinical care area in which the infusion pump is located.

17. The method of claim 16, wherein the clinical care area is determined based on an identification data associated with the infusion pump.

18. The method of claim 10, further comprising transmitting the alarm condition to a third computing system different from the second computing system based on a determination that the transmission to the second computing system failed.

\* \* \* \* \*